(12) United States Patent
Ebensen et al.

(10) Patent No.: US 10,918,733 B2
(45) Date of Patent: Feb. 16, 2021

(54) LIPOPEPTIDE- AND LIPOPROTEIN-CONJUGATES AND ITS USE

(75) Inventors: Thomas Ebensen, Langenhagen (DE); Carlos Alberto Guzman, Wolfenbuettel (DE); Michael Morr, Wolfenbuettel (DE); Werner Tegge, Braunschweig (DE)

(73) Assignee: HELMHOLTZ-ZENTRUM FUER INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 13/519,336

(22) PCT Filed: Dec. 28, 2010

(86) PCT No.: PCT/EP2010/070776
§ 371 (c)(1),
(2), (4) Date: Jun. 27, 2012

(87) PCT Pub. No.: WO2011/080259
PCT Pub. Date: Jul. 7, 2011

(65) Prior Publication Data
US 2013/0039939 A1    Feb. 14, 2013

(30) Foreign Application Priority Data
Dec. 28, 2009   (EP) .................................... 09016050

(51) Int. Cl.
*A61K 47/60*   (2017.01)
*A61K 47/64*   (2017.01)
*A61K 47/54*   (2017.01)

(52) U.S. Cl.
CPC .......... *A61K 47/646* (2017.08); *A61K 47/543* (2017.08); *A61K 47/60* (2017.08)

(58) Field of Classification Search
None
See application file for complete search history.

(56) References Cited

U.S. PATENT DOCUMENTS 5,993,823 A * 11/1999 Boutillon ......... A61K 47/48038
424/184.1
2007/0231335 A1* 10/2007 Beutler et al. ............. 424/165.1

FOREIGN PATENT DOCUMENTS

WO   2004/014956   2/2004

OTHER PUBLICATIONS

Nisbet et al, The Complete Amino-Acid Sequence of Hen Ovalbumin, Eur. J. Biochem. 115, 335-345 (1981).*
Babu et al, Priming for virus-specific CD8+ but not CD4+ cytotoxic T lymphocytes with synthetic lipopeptide is influenced by acylation units and liposome encapsulation, Vaccine 1995 vol. 13 No. 17 1669-1676.*
Shaw, A.S., et al. Short Related Sequences in the Cytoplasmic Domains of CD4 and CD8 Mediate Binding to the Amino-Terminal Domain of the p56lck Tyrosine Protein Kinase, Molecular and Cellular Biology, May 1990, p. 1853-1862.*
Delgado C, et al "The uses and properties of PEG-linked proteins," Crit Rev Ther Drug Carrier Syst. 1992;9(3-4):249-304. (Year: 1992).*
Deliyannis et al.; "Intranasal lipopeptide primes lung-resident memory CD8+ T cells for long-term pulmonary protection against influenza"; European Journal of Immunology, vol. 36, No. 3, Jan. 24, 2006, pp. 770-778.

* cited by examiner

Primary Examiner — Thomas S Heard
(74) Attorney, Agent, or Firm — W&C IP

(57) ABSTRACT

The present invention relates to new lipopeptide- and lipoprotein molecules and lipopeptide- and lipoprotein-conjugates. In particular, the present invention relates to new lipopeptide- and lipoprotein molecules and lipopeptide- and lipoprotein-conjugates comprising a lipid-containing moiety representing an adjuvant moiety, a peptide or protein moiety whereby said peptide or protein moiety represents at least one antigenic structure, the antigen-moiety, and, optionally, a conjugate moiety, preferably a monodisperse polyethyleneglycol unit.

Figure 1:
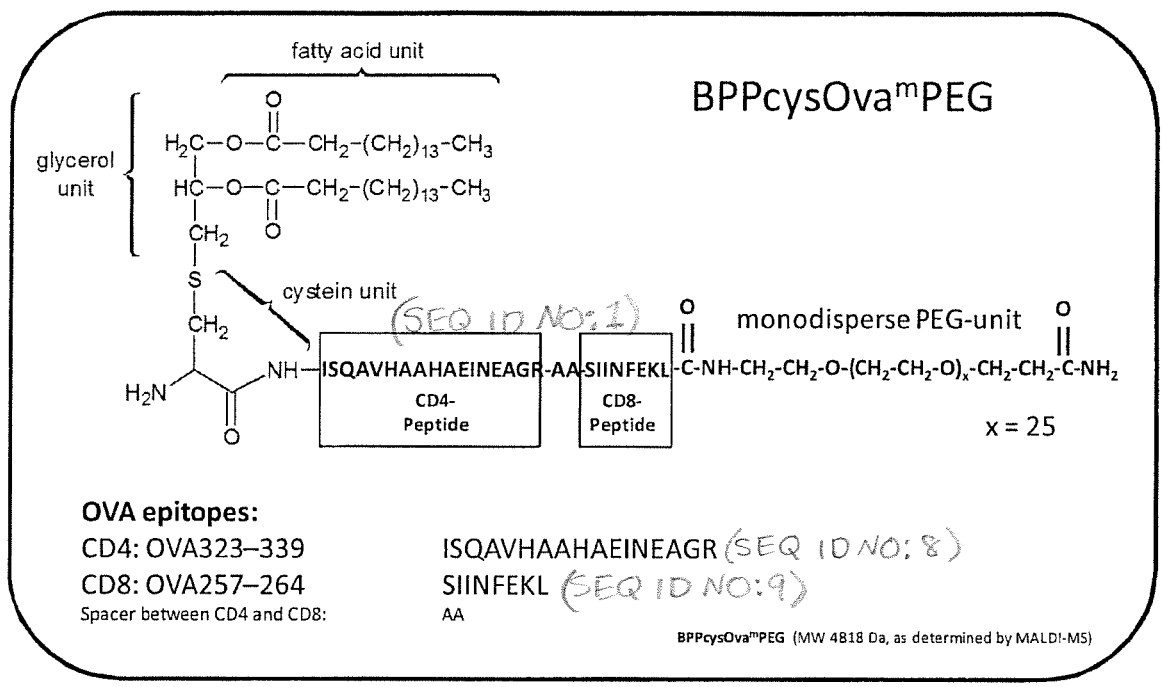

Said compounds are particularly useful for therapeutic or prophylactic vaccination by mucosal or systemic administration, preferably mucosal and systemic vaccination. That is, the present invention relates in another aspect to pharmaceutical compositions comprising the compounds according to the present invention, in particular, said pharmaceutical compositions are vaccines. In addition, said pharmaceutical compositions are useful for the prophylaxis or treatment of infectious diseases, inflammatory and autoimmune diseases, cancer, allergies or for the control of fertility in human or animal populations.

13 Claims, 8 Drawing Sheets
Specification includes a Sequence Listing.

BPPcysHA-NP$^m$PEG
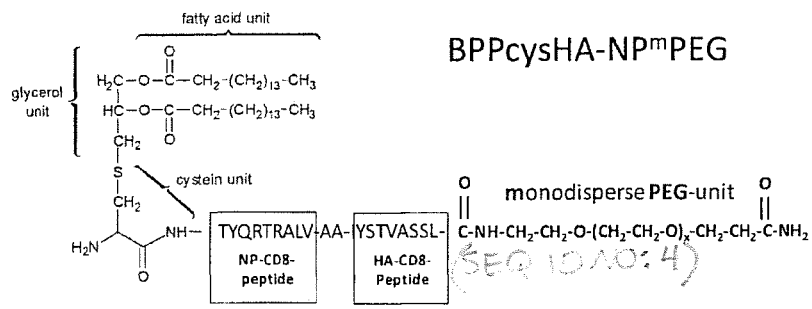
NP have sequence identities of 94%, with the H1N1 PR/8/34 NP and include the immunodominant Class I epitope spanning amino acids 147–155 (TYQRTRALV).
Fig. 10B
BPPcysE3$^m$PEG
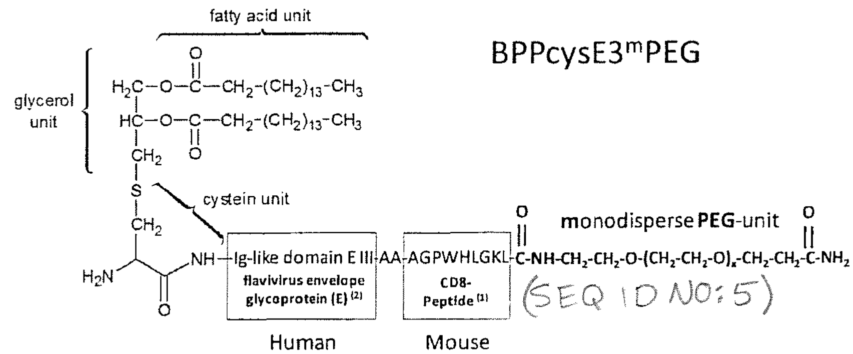
Fig. 10C
BPPcysHB1$^m$PEG
BPPcysHB2$^m$PEG
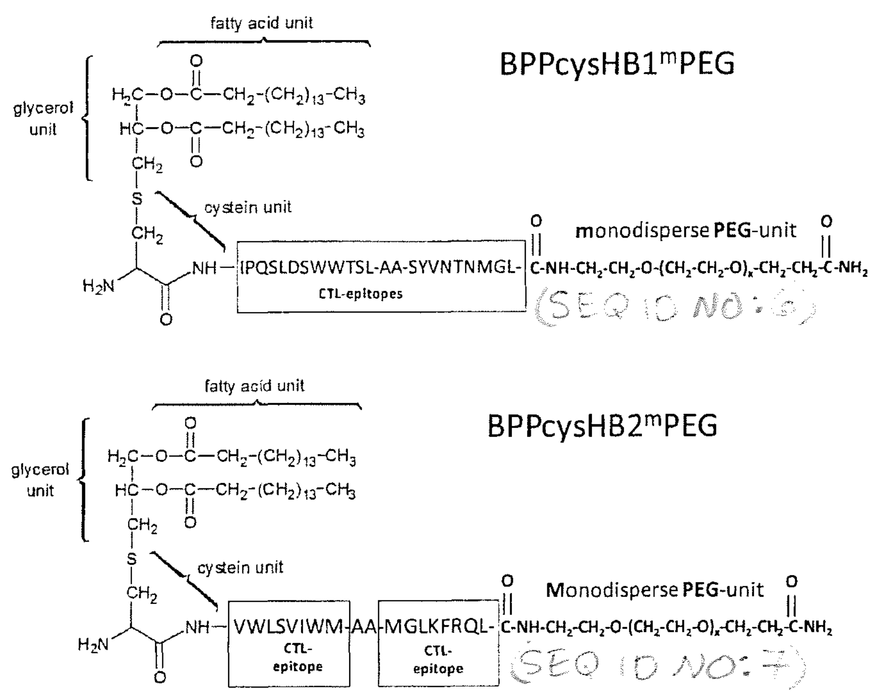
Fig. 10D

SEQUENCE LISTING

```
<160> NUMBER OF SEQ ID NOS: 9

<210> SEQ ID NO 1
<211> LENGTH: 27
<212> TYPE: PRT
<213> ORGANISM: artificial
<220> FEATURE:
<223> OTHER INFORMATION: synthetic peptide

<400> SEQUENCE: 1

Ile Ser Gln Ala Val His Ala Ala His Ala Glu Ile Asn Glu Ala Gly
1               5                   10                  15

Arg Ala Ala Ser Ile Ile Asn Phe Glu Lys Leu
            20                  25

<210> SEQ ID NO 2
<211> LENGTH: 22
<212> TYPE: PRT
<213> ORGANISM: artificial
<220> FEATURE:
<223> OTHER INFORMATION: synthetic peptide HA-S1

<400> SEQUENCE: 2

Ser Phe Glu Arg Phe Glu Ile Phe Pro Lys Glu Ala Ala Ile Tyr Ser
1               5                   10                  15

Thr Val Ala Ser Ser Leu
            20
```

```
<210> SEQ ID NO 3
<211> LENGTH: 24
<212> TYPE: PRT
<213> ORGANISM: artificial
<220> FEATURE:
<223> OTHER INFORMATION: synthetic peptide HA-S2

<400> SEQUENCE: 3

His Asn Thr Thr Lys Gly Val Thr Ala Ala Cys Ser His Ala Ala Ile
1               5                   10                  15

Tyr Ser Thr Val Ala Ser Ser Leu
            20

<210> SEQ ID NO 4
<211> LENGTH: 20
<212> TYPE: PRT
<213> ORGANISM: artificial
<220> FEATURE:
<223> OTHER INFORMATION: synthetic peptide HA-NP

<400> SEQUENCE: 4

Thr Tyr Gln Arg Thr Arg Ala Leu Val Ala Ala Ile Tyr Ser Thr Val
1               5                   10                  15

Ala Ser Ser Leu
            20

<210> SEQ ID NO 5
<211> LENGTH: 11
<212> TYPE: PRT
<213> ORGANISM: artificial
<220> FEATURE:
<223> OTHER INFORMATION: synthetic peptide E3

<400> SEQUENCE: 5

Ala Ala Ala Gly Pro Trp His Leu Gly Lys Leu
1               5                   10

<210> SEQ ID NO 6
<211> LENGTH: 23
<212> TYPE: PRT
<213> ORGANISM: artificial
<220> FEATURE:
<223> OTHER INFORMATION: synthetic peptide HB1

<400> SEQUENCE: 6

Ile Pro Gln Ser Leu Asp Ser Trp Trp Thr Ser Leu Ala Ala Ser Tyr
1               5                   10                  15

Val Asn Thr Asn Met Gly Leu
            20

<210> SEQ ID NO 7
<211> LENGTH: 18
<212> TYPE: PRT
<213> ORGANISM: artificial
<220> FEATURE:
<223> OTHER INFORMATION: synthetic peptide HB2

<400> SEQUENCE: 7

Val Trp Leu Ser Val Ile Trp Met Ala Ala Met Gly Leu Lys Phe Arg
1               5                   10                  15

Gln Leu

<210> SEQ ID NO 8
<211> LENGTH: 17
```

```
<212> TYPE: PRT
<213> ORGANISM: artificial
<220> FEATURE:
<223> OTHER INFORMATION: synthetic peptide

<400> SEQUENCE: 8

Ile Ser Gln Ala Val His Ala Ala His Ala Glu Ile Asn Glu Ala Gly
1               5                   10                  15

Arg

<210> SEQ ID NO 9
<211> LENGTH: 8
<212> TYPE: PRT
<213> ORGANISM: artificial
<220> FEATURE:
<223> OTHER INFORMATION: synthetic peptide

<400> SEQUENCE: 9

Ser Ile Ile Asn Phe Glu Lys Leu
1               5
```

LIPOPEPTIDE- AND LIPOPROTEIN-CONJUGATES AND ITS USE

The present invention relates to new lipopeptide- and lipoprotein molecules and lipopeptide- and lipoprotein-conjugates. In particular, the present invention relates to new lipopeptide- and lipoprotein molecules and lipopeptide- and lipoprotein-conjugates comprising a lipid-containing moiety representing an adjuvant moiety, a peptide or protein moiety whereby said peptide or protein moiety represents at least one antigenic structure—the antigen-moiety—, and, optionally, a conjugate moiety, preferably a monodisperse polyethyleneglycol unit.

Said compounds are particularly useful for therapeutic or prophylactic vaccination by mucosal or systemic administration, preferably for mucosal and systemic vaccination. That is, the present invention relates in another aspect to pharmaceutical compositions comprising the compounds according to the present invention, in particular, said pharmaceutical compositions are vaccines. In addition, said pharmaceutical compositions are useful for the prophylaxis or treatment of infectious diseases, inflammatory and autoimmune diseases, cancer, allergies or for the control of fertility in human or animal populations.

PRIOR ART

Infectious diseases are the major cause of morbidity and mortality, accounting for a third of the deaths which occur in the world each year. In addition, infectious agents are directly responsible for at least 15% of new cancers, and they also seem to be involved in the pathophysiology of several chronic diseases (e.g. inflammatory, vascular and degenerative). Traditional infectious diseases are also highly expensive in terms of health-associated costs of infected patients and loss in productivity at work.

The main strategies used to prevent infectious diseases are therapy and prophylaxis. Between these two options, vaccination has become the most cost-effective measure to combat infectious agents. However, there are still many diseases for which vaccines are not yet available or the available vaccines are not completely satisfactory due to low efficacy, high reactogenicity, poor stability and/or high costs. Thus, there is an urgent need for both new and improved vaccines. Despite the fact that vaccines have traditionally been used for the prophylaxis of infectious diseases, new knowledge suggests that they are also a powerful tool for the immunotherapy of transmissible diseases (e.g. viral hepatitis, *Helicobacter pylori* infections, herpes virus infections, Dengue fever etc.). In addition, vaccines can be used for the immune-therapy or immune-prophylaxis of autoimmune diseases, inflammatory diseases, tumours, allergies and for the control of fertility in human and/or animal populations. In particular the last application seems to require the elicitation of efficient mucosal responses at the level of the reproductive tract.

Most infectious diseases are either restricted to the mucosal membranes or the etiologic agents need to transit the mucosa during the early steps of the infection. Therefore, it is desirable to obtain not only a systemic, but also a local mucosal immune response as a result of vaccination, thereby blocking both infection (i.e. colonization) and disease development. This may result in a more efficient protection against infection, facilitating also the eradication of diseases for which humans are the only reservoirs (i.e. blocking transmission to susceptible hosts). Due to the apparent compartmentalization of the systemic and mucosal immune system, parenterally administered vaccines are less effective in protecting against mucosal pathogens. In fact, parenterally-administered vaccines mainly stimulate systemic responses, whereas vaccines administered by a mucosal route mimic the immune response elicited by natural infections and can lead to efficient mucosal and systemic responses. Thus, administration of immunogens through the mucosal route is required to achieve full protection. The administration of vaccines by a mucosal route is also associated with lower rates of side effects, higher acceptance by the public, and better compliance of vaccination protocols (i.e. increment in the overall efficacy), simpler administration logistics and lower delivery costs, being particularly suitable for mass immunization programmes. However, the compartmentalisation at the level of the mucosal immune system is relative. In fact, in contrast to what observed following intra-nasal vaccination, oral or intra-rectal immunisation will not necessarily stimulate efficient responses in the genitourinary and/or respiratory tracts.

Unfortunately, the delivery of antigens by the mucosal route is associated with a major problem, namely that antigens delivered by this route are generally poorly immunogenic. This is the result of different mechanisms, such as (i) accelerated antigen elimination by the non specific host clearance mechanisms (e.g. ciliar activity, peristaltism), (ii) antigen degradation by local enzymes, (iii) antigen alteration and/or structural modification as a result of extreme pH (e.g. acidic in the stomach, alcaline in the intestine), (iv) poor antigen penetration through the mucosa, and (v) limited access of vaccine antigens to antigen presenting cells. To overcome these problems, different strategies have been used, such as antigen entrapment or association with physical or biological particles (e.g. microparticles, nanoparticles, bacterial ghosts), the use of virus-like-particles, the use of liposomes or ISCOMS, the use of transgenic plants, antigen production by attenuated viral or bacterial carriers acting either as conventional vectors or as carriers for nucleic acid vaccines and/or their administration with mucosal adjuvants. However, despite the heavy body of experimental evidence generated in pre-clinical studies during the last years, almost a few candidates have been transferred to the vaccine development pipeline.

Current vaccine and immunotherapy technology faces ongoing challenges in both efficacy and practicality: many diseases cannot yet be addressed by vaccination, and several vaccines that do function well require multiple injections, which is a substantial limitation in various parts of the world. One possible key to develop the next generation of vaccines is the ability to deliver antigen to dendritic cells (DCs) more specifically and induce the subsequent activation of T-cell immunity. However, antigen delivery to, and activation of DCs is a complex problem, involving antigen transport to DC-rich areas, DC binding and antigen uptake, and antigen processing and presentation. Moreover, antigen-targeting as well as cross-presentation must be considered when developing vaccines. In this connection, cross-presentation refers to the display of peptides derived from exogenous antigens on MHC class I molecules. Cross presentation is important for effective immune responses to tumours and viral infections, see e.g. McDonnell A. M., et al., 2010, Clin Dev Immunol. 2010; 2010:539519. Vaccine strategies combined with, or without, adjuvants have been established to eradicate various bacterial and viral pathogens. The conjugation of weakly-immunogenic tumour-derived proteins or other pathogen-associated antigens to highly-immunogenic carrier proteins has long been utilized as a tool for improving immune responses. Such vaccines have recently been tested in phase 3 clinical trials targeting non-Hodgkin's B cell lymphoma. However, these vaccines, composed of tumor-specific immunoglobulin protein linked to keyhole limpet hemocyanin using glutaraldehyde, largely failed to show efficacy. Nevertheless, substituting a sulfhydryl-based linker cleavable in lysosomes markedly augments the efficacy of these vaccines, offering heightened antibody and CTL responses. Another example showed that close physical contact between the CpG ODN (oligodesoxynucleotides) and the immunogen has improved the resultant of humoral and/or cellular immune responses, culminating in enhanced protective immunity in rodent and primate challenge models. Clinical studies indicate that CpG ODN is safe and well-tolerated when administered as adjuvants to humans, and that they can support increased vaccine-specific immune responses.

In WO 2004/014956 immunogenic lipopeptides are described comprising T-helper and B-cell epitopes. As demonstrated therein, the solubility of lipopeptides having the lipid attached between the two epitopes were soluble in concentrations of at least 8 mg/ml whereas constructs in which the lipid was attached to the N-terminus of sequences of both epitopes in linear form formed opalescent solutions at concentrations as low as 0.25 mg/ml. Hence, this application as well as WO 2006/084319 teach the use of lipopeptides wherein the lipid is placed between two different epitopes. In Deliyannis et al., Eur. J. Immunol, 2006, 36, 770-778, lipopeptides of the same type are described wherein the epitopes at both ends of the lipids are composed of CD4 and CD8 epitopes, respectively. However, the document is silent about any effects on the toll-like-receptor 6 or on regulatory T-cells. In addition, no significant difference between the lipopeptide and the peptide not containing the lipid moiety has been demonstrated. Further, it is emphasized that the lipopetide of CD4 and CD8 epitope do no elicit any anti-viral antibodies.

Hence, there is still a need in the prior art to provide new compounds useful as vaccines and pharmaceutical compositions to prevent and treat various diseases. In particular, there is still a need for compounds and molecules combining the activity of eliciting and enhancing immune responses. That is, there is a need for pharmaceutical compositions which can elicit a strong immune response which represents a balanced or adjusted immune response involving both, humoral and cellular components, thus, allowing effective prophylaxis or treatment of various diseases and conditions, specifically of infectious diseases or cancer. There is still a need for compounds eliciting an antibody based immune response and a cytotoxic T-cells based immune response. Furthermore, the bioavailability of said compounds should be good with excellent stability and activity, thus, allowing to reduce the dosage and to increase bio-safety of the compounds. In particular, vaccines are required which provides a good protection by having fewer side effects.

Hence, the present invention relates in a first aspect to new compounds which are lipopeptide- and lipoprotein molecules and lipopeptide- or lipoprotein-conjugates able to elicit and/or enhance and/or modulate an immune response in an individual or subject. In particular, the invention is based on developing a new compound combining the ability of eliciting an immune response by containing antigenic structures as well as having the ability of enhancing the immune response in an individual acting as an adjuvant, i.e. having adjuvant activity. The compounds according to the present invention are composed of at least one adjuvant moiety, at least one antigen moiety and, optionally, a conjugate moiety.

DESCRIPTION OF THE INVENTION

The technical problem is solved by the provision of the embodiments as characterised in the claims and as outlined in detail in the following:

In a first aspect, the present invention relates to lipopeptide-compounds or lipoprotein-compounds according to claim 1, or lipopeptide-conjugate compounds or lipoprotein-conjugate compounds according to formula I

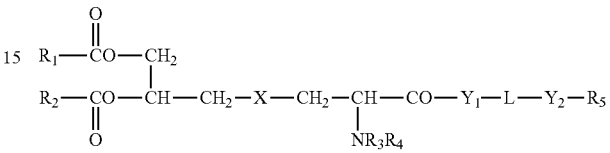

(I)

wherein $R_1$ and $R_2$ can be identical or different and are selected from $C_{7-25}$ alkyl, $C_{7-25}$ alkenyl or $C_{7-25}$ alkynyl;
$R_3$ and $R_4$ can be identical or different and are selected from hydrogen or $C_{1-6}$ alkyl group;
X is selected from S, O or $CH_2$;
$Y_1$ is an amino acid sequence of 6 to 30 amino acid residues;
$Y_2$ is an amino acid sequence of 6 to 30 amino acid residues;
L is absent or is an amino acid sequence of 1 to 10 amino acid residues;
$R_5$ is hydrogen or a covalently linked conjugate moiety comprising polyalkylene glycol units of the formula II:

$$Z_1\text{---}[(CHR_6)_n\text{---}O)]_x\text{---}(CH_2)_2\text{---}Z_2 \quad (II)$$

where $Z_1$ is a hydrocarbon or a $NR_3$ group, $R_6$ is independently any one of hydrogen, OH, $C_{1-6}$ alkyl group, $OR_7$ or $COR_8$;
$R_7$ is independently any one of hydrogen or $C_{1-6}$ alkyl group;
$R_8$ is independently any one of hydrogen, OH, $OR_7$ or $NR_9R_{10}$;
$R_9$ and $R_{10}$ are independently any one of hydrogen or hydrocarbon which may contain heteroatom(s) and which may form a ring;
x is an integer of 1 to 100;
n is independently an integer of 1 to 10;
$Z_2$ is a hydrogen or a hydrocarbon which may contain heteroatom(s), preferably an amid goup;
or salts or solvates thereof, wherein $Y_1$ represents a CD4 epitope and $Y_2$ represents a CD8 epitope of the same or different antigen, able to elicit an immune response in an individual, or vice versa, namely, $Y_1$ is a CD8 epitope and $Y_2$ is a CD4 epitope.

Herein it is demonstrated for the first time that compounds according to the present invention, namely, the conjugation of the active moiety of MALP-2 representing a known adjuvant moiety, with antigen specific peptides (e.g. Ovalbumin, peptides containing antigenic structures of CD4 and/or CD8 epitopes and/or B-cell epitopes) is able to target antigen presenting cells, suchas dendritic cells or macrophages, as well as antigen-specific CD4 and CD8 T cells. By conjugation of PEG the solubility and stability of the novel compounds is enhanced further in a preferred embodiment. Furthermore, it is possible to reduce the antigen and adjuvant concentration without loss of immunogenicity, which is of interest in terms of dose savings and adverse side effects occurring after vaccination. Using the novel compound according to the present invention, like the BPPcyspeptide$^m$-PEG compound described below, it is possible to modulate the immune response by antigen targeting. E.g. the T-cell epitopes of the ovalbumin representing a well known and accepted model antigen engineered to the active moiety of MALP-2 (so called BPPcys) molecules can be targeted to antigen presenting cells, such as macrophages or dendritic cells. Ovalbumin derived epitopes (e.g. CD4 and CD8 specific peptides) and its presentation by dendritic cells in vitro and its immunogenicity in vivo is shown herein. Using these antigen epitopes (e.g. peptides) it is possible to induce optimal immune responses.

That is, the invention refers to the use of the lipopeptide- and lipoprotein molecules and the lipopeptide- and lipoprotein-conjugate compounds according to the present invention, e.g. of BPPcyspeptide'''PEG, as adjuvant-antigen molecules for therapeutic or preventive vaccination and/or treatment of infectious diseases, inflammatory diseases, autoimmune diseases, tumours, allergies or for the control of fertility in human or animal populations. More specifically the invention refers to the use the lipopeptide- and lipoprotein molecules and the lipopeptide- and lipoprotein-conjugate compounds according to the present invention, e.g. of BPPcyspeptide'''PEG, as a pharmaceutical which can be administered systemically or mucosally (e.g. for intranasal, intra-NALT [nasal associated lymphoid tissue], intra-conjuctival, oral, intra-rectal, intra-vaginal or intra-urethral administered vaccines), in immunisation protocols aimed at the prevention or therapy of infectious diseases, inflammatory and autoimmune diseases, cancer, allergies or for the control of fertility in human or animal populations. As proof of principle in preliminary studies the CD4 and CD8 specific peptides of the model antigen ovalbumin (Ova) has been used, the compound termed as BPPcysOva'''PEG, see FIG. 1. In this connection, it is noted that term "'''PEG" refers to monodisperse polyethylenglycol.

In this connection, the term "monodisperse" refers to components having the same size or mass in contrast to "polydisperse" components which have an inconsistent size and mass.

As shown in the examples, the presence of the molecules according to the present invention result in the promotion of an efficient processing and presentation of antigens by professional antigen presenting cells, particularly macrophages, dendritic cells, B cells and lymphatic or vascular endothelial cells, by either a direct effect or indirectly by promoting the establishment of an appropriate local microenvironment. This in turn leads to the elicitation of not only systemic, but also mucosal immune responses at local (site of immunization) and/or distant mucosal sites. The immune responses stimulated are humoral and/or cellular (e.g. T helper, cytotoxic T lymphocytes and B-cells) as shown by the presence of appropriate T-cells, cytokines and antigen-specific antibodies. The compounds and conjugates according to the present invention allow cross-presentation of MHC class I restricted antigens to naive CD8+ T cells as shown in the examples. Further, the lipid moiety enables antigen targeting to dendritic cells, e.g. based on TLR2 and TLR6 interactions. Thus, it is possible to provide specific and effective vaccines using the compounds according to the present invention.

Thus, the present invention is generally concerned with the provision of new lipopeptide- and lipoprotein molecules and lipopetide- and lipoprotein-conjugates or salts or solvates thereof, useful as immunomodulatory compounds, in particular, as vaccines, like mucosal vaccines. Furthermore, the present invention relates to new pharmaceuticals comprising the lipopeptide- and lipoprotein molecules and the conjugates as described herein with pharmaceutically acceptable carrier(s), optionally together with additional active ingredients for the treatment of various diseases as identified in the following.

That is, the present invention relates to the provision of the use of specific compounds or conjugates useful as immunomodulators in therapeutic or prophylactic vaccination. Said compounds and conjugates are useful as systemic and are particularly useful as mucosal pharmaceuticals being applied via the mucosa of the individual.

The present inventors now found that Bisacyloxypropylpeptides. i.e. adjuvant-antigen-molecules, and its conjugates, i.e. adjuvant-antigen-conjugate molecules, are particularly useful as pharmaceuticals in vaccines for therapeutic or prophylactic vaccination. In particular, compounds as described herein demonstrate the applicability as parenteral adjuvants and, in particular, as mucosal adjuvants at low doses.

As used herein, the term "adjuvant" means substances which—in the art—are added and/or co-formulated in an immunization to the active antigen, i.e. the substance which provokes the desired immune response, in order to enhance or elicit or modulate the humoral and/or cell-mediated (cellular) immune response against the active antigen. Preferably, the adjuvant moiety present in the compounds according to the present invention is also able to enhance or elicit the humoral and cellular immune response.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of a drug, among others.

As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes, polyoma-like particles, attenuated vaccines and virus-like particles.

As used herein, the term "conjugate moiety" refers to a moiety which is linked to the bisacyloxypropylpeptide residue. The conjugate moiety aims to increase the applicability of the compounds disclosed herein. As used herein, the term "pegylated" refers to the conjugation of the adjuvant and antigen moiety with conjugate moiety(ies) containing at least one polyalkylene unit as defined herein. In particular, the term pegylated refers to the conjugation of the adjuvant-antigen moiety with a conjugate moiety having at least one polyethylene glycol units.

As used herein, the term "mucosal" refers to mucosal surface from the body such as the nasal, oral, gastro-enteric, rectal, urinary, conjunctial, glandular, e.g. mammary gland, epithelial mucous.

As used herein, the term "antigenic structure" or "antigen" refers to a structure capable of causing a cellular and/or humoral immune response. The antigenic structure, also known as CD4 epitope and/or CD8 epitope is the part of the antigen, which is presented by the MHC class I or II or MHC like molecules. Further, the B-cell epitope or antigenic structure represents the part of an antigen recognized by antibodies directed against said antigen As used herein, the term "modulate an immune response" refers to any change of the present state of the immune response. The immune response may be modulated insofar that the response is elicited and/or a pre-existing immune response is enhanced or decreased. In addition, the immune response may be modulated by shifting the immune response from a more humoral to a more cellular immune response or vice versa. Further, the immune response may be modulated by switching or redirecting the response from a Th1 to Th2 or Th3 response or vice versa, in particular a balanced Th1/Th2 response. In addition, the modulation of the immune response may encompass the activation or enhancement of the innate immune response.

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

As used herein, the term "carrier" refers to a diluent, adjuvant, excipient, or vehicle.

As used herein, the term alkyl alkenyl or alkynyl refer to hydrocarbon groups which may be linear or branched or cyclic. Further, the term" which may be substituted" refer to substituents selected from halogen, OH, COOH, O—$C_1$-$C_6$-alkyl, COO—$C_1$-$C_6$-alkyl, COOH, $CONH_2$, CN, CONH($C_1$-$C_6$-alkyl), CON($C_1$-$C_6$-alkyl)$_2$.

The polyalkylene glycol unit mentioned above may preferably contain at least two subunits of ethylene glycol, propylene glycol or butylene glycol or combinations thereof. The chain length of each of the polyalkylene glycol units may be in the range of 1 to 100 subunits, preferably, 2 to 50 subunits, like 20 to 40 subunits, particularly in the range of 25 to 30 subunits, like 25, 26, 27, 28, 29, or 30.

Particularly preferred the polyalkylene glycol subunit is a polyalkyleneglycol-carbonyl-residue wherein the alkylene moiety is an ethylene or propylene moiety.

Hence, the conjugated form as defined herein allows increasing the solubility in hydrophilic solvents and hydrophilic environment. Furthermore, the conjugate moiety allows protecting the adjuvant-antigen moiety, i.e. the active mucosal adjuvant moiety, against enzymatic degradation, structural modification due to change of the pH, mechanical removal, etc. Thus, primarily the stability of the compound is increased. Another beneficial effect of conjugation is to increase the retention time in the individual, e.g. to delay the renal excretion, while being well-tolerated, e.g. being non immunogenic, by said organism. Thus, the conjugate according to the present invention display an improved bioavailability while allowing reduction of the dosage necessary to elicit the desired effect.

In addition, the conjugates according to the present invention allow providing the antigen and the adjuvant in a well-defined dosage, in particular when using monodisperse conjugate moieties. In addition, also possible and sometimes desired, the use of vehicles is not necessary. Moreover, the problems of preparing two components of the ready to use vaccine, as it is the case for the H1N1 drug presently used for immunising individuals, is not required since both components, the antigen and the adjuvant component, are present in the molecules and conjugates according to the present invention.

The conjugate may be a branched compound wherein each arm contains a polyalkylene glycol unit. Particularly preferred are conjugate moieties wherein the polyalkylene glycol unit is a polyethylene, polypropylene or polybutylene glycol unit.

In a particularly preferred embodiment, the compound moiety being covalently linked with the conjugate moiety is a branched moiety wherein at least two arms containing polyethylene glycol units having 3 to 5 ethylene glycol subunits and a methoxy group at the free end of the polyethylene group. In particular, the branched moiety comprises 4 or 6 or 8 arms each having 3 ethylene glycol subunits and a methoxy group at the free end of the polyethylene group.

The so-called PEGylation method, in which the biopharmaceutical drug is coupled with polyethylene glycol (PEG) represents a preferred embodiment of the In present invention resulting in e.g. the BPPcyspeptide$^m$PEG molecules described herein. The traditional PEGylation chain-like structures are attached to the drug molecule. Coupling with PEG molecules results in considerably greater protease stability, a significant decrease in immunogenicity and a perceptible delaying of renal excretion. The PEG masking reagent support the protection of the drug to withstand attacks by the immune system and enzymatic degradation processes, reach its destination unimpeded and exert its therapeutic effect efficiently. In comparison to the common PEG reagents (chain-like structure, polydisperse, cross-links possible, structurally determined fluctuations in quality at any time) the compounds according to the BPPcysOva$^m$PEG showed a linear structure with defined size. In the present invention the conjugated $^m$PEG used can be of branched or linear structure. Using $^M$PEG with defined size gives reproducible quality various drug-specific optimization possibilities. For example, the BPPcysOva$^m$PEG compound gives the possibility to analyze the compounds by HPLC analysis because the compound is monodisperse resulting in one single signal with a MW of 4818 Da as shown in FIG. 1.

Particularly preferred embodiments of the adjuvant-antigen-conjugate or the lipopeptide- and lipoprotein-conjugate according to the present invention are shown in FIG. 10A-D (Seq. ID. Nos. 2 to 7). The compounds contain CD4 and CD8 antigenic structures derived from influenza, Dengue fever, and hepatitis B or C, respectively.

The lipopeptide- and lipoprotein molecules and the lipopetide- or lipoprotein-conjugates described herein may be in the form of pharmaceutically acceptable non-toxic salts thereof. Salts include acid added salts, such as salts with inorganic acids (e.g. hydrochloric acid, sulphuric acid, nitric acid and phosphoric acid) or with organic acids (e.g. acetic acid, propionic acid, maleic acid, olec acid, palmitic acid, citric acid, succinic acid, tartaric acid, fumaric acid, glutamic acid, panthothenic acid, laurylsulfonic acid, methanesulfonic acid and phthalic acid).

The conjugates may be in the form of solvates thereof (e.g., hydrates).

In addition, the conjugates may form salts with cationic ions, like metallic ions, in particular alkali or alkaline earth metal ions, or $NH_4^+$.

Preferably the lipopeptide- and lipoprotein-conjugate according to the present invention is a S-[2,3-bis(acyloxy)-(2S)-propyl]-peptide-conjugate, preferably, a S-[2,3-bis(palmitoyloxy)-(2S)-propyl]-peptide-conjugate.

In another embodiment the conjugate is a S-[2,3-bis(acyloxy)-(2R)-propyl]-peptide-conjugate, preferably, a S-[2,3-bis(palmitoyloxy)-(2R)-propyl]-peptide-conjugate.

Preferably, $Y_1$ and/or $Y_2$ contain of from 6 to 30 amino acid residues, like of from 8 to 25 aa, preferably, of from 8 to 16, e.g. for CD8 epitopes, the size is of from 8 to 14 aa while for CD4 epitopes, the size is of from 10 to 20 aa.

Further, L is preferably an amino acid sequence of 1 to 3 amino acid residues, in particular of 2 amino acid residues. Preferably, L is composed of the amino acid residue alanine, Ala or A.

Moreover, the lipopeptide- or a lipoprotein compounds or the lipopeptide- or a lipoprotein-conjugate is a lipopeptide- or lipoprotein-compound or -conjugate having a bisacyloxy-propyl cystein adjuvant-antigen moiety with X=S.

In addition, the lipopeptide- or a lipoprotein-compound or the lipopeptide- or lipoprotein-conjugate according to the present invention is a compound or conjugate wherein $Y_1$ and $Y_2$ are present whereby $Y_1$ and $Y_2$ may optionally be spaced apart by L and wherein $Y_1$ and $Y_2$ represent antigenic structures able to elicit an immune response in an individual.

The lipopeptide- or a lipoprotein-compound or the lipopeptide- or lipoprotein-conjugate is a compound or conjugate wherein $Y_1$ represents a CD4 epitope and $Y_2$ represents a CD8 epitope of the same or different antigen able to elicit an immune response, or vice versa, namely, $Y_1$ is a CD8 epitope and $Y_2$ is a CD4 epitope. In particular, the compounds and conjugates according to the present invention enables cross presentation by dendritic cells, thus, allowing effective immune responses, e.g. immune responses to tumours and viral infections.

The lipopeptide- or a lipoprotein-compound or the lipopeptide- or lipoprotein-conjugate according to the present invention is preferably a compound or conjugate wherein $R_1$ or $R_2$ represents $C_{11}$-$C_{17}$ alkyl or $C_{11}$-$C_{17}$ alkenyl groups, preferably, $R_1$ and $R_2$ are identical being a $C_{15}$ alkyl group. Said alkyl, alkenyl or alkynyl groups may be substituted.

In a further embodiment, the lipopeptide- or lipoprotein-conjugate is characterized in being a conjugate wherein n is an integer of 2, 3 or 4, preferably 2, and x is independently therefrom an integer of 15 to 35, preferably 20 to 30, like 25, 26, 27, 28, 29, 30.

Particularly preferred the lipopeptide- or lipoprotein-conjugate according to the present invention is a conjugate wherein $R_5$ represents a monodisperse polyethyleneglycol unit.

The lipopeptide- or lipoprotein-conjugate according to the present invention is a lipopeptide or a lipopeptide conjugate wherein $Y_1$ and $Y_2$ represent CD4 and CD8 epitopes of the following sources: hepatitis B or C, HIV or other virus, Dengue fever inducing virus, influenza or vaccinia, cancer, etc.

The lipopeptide- and lipoprotein molecules and the lipopeptide- and lipoprotein-conjugates as described above can additionally used as an immunomodulator in a pharmaceutical composition for preventing or treating infectious diseases, cancers, tumours, autoimmune diseases or allergies, or chronic or acute inflammatory processes or to control fertility in human or animal populations.

The synthesis of conjugates may be conducted by methods known to the person in the art. For example, a hydroxyl group may be converted into a halogen residue, e.g. Cl. Br, I and this residue can react with modified conjugates having a free amino-group. For example, synthesis of conjugates having a polyalkylene glycol moiety representing the conjugate moiety are described in Veronese F. M., Biomaterials 22 (2001), 405-417 and Kodera Y., et al., Prog. Polym. Sci. (1998), 23, 1233-1271 which are incorporated herein by reference.

In a preferred embodiment, the molecule(s) or conjugate(s), or the salts or solvates thereof are useful as mucosal pharmaceuticals, like vaccines, in particular, for intranasal, intra NALT, oral, intra-rectal, conjunctival, intravaginal, intrathecal, intrabronchial, intrapulmonary, or intraurethral administration, administration into the milk ducts of the breast or by inhalation. Further, the vaccine or pharmaceutical composition may be administered directly into the organ, like into the liver or the spleen or may be applied intralymphatically.

Particularly preferred is the intranasal administration or the administration by inhalation using suitable aerosol formulations. Aerosol formulations useful for administration of vaccines are known in the art.

The compounds, the conjugates or its salts or solvates thereof are also suitable as systemic pharmaceuticals. Thus, the pharmaceuticals, like the vaccines, as described herein are also applicable as parenteral pharmaceuticals, in particular, in subcutaneous, topical (transcutanous vaccination), intravenous, intradermal, topical or intramuscular administration.

The compound(s) or conjugate(s), or the salts or solvates thereof containing the active vaccination component (e.g. the antigenic structure) are provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastro-intestinal tract.

Thus, the compounds or conjugates according to the present invention direct the immune response towards a balanced immune response including a humoral and cellular CD4 and CD8 as well as a B-cell immune response.

In another embodiment, the present invention relates to methods of treating individuals afflicted with a disease or condition that can be treated by modulating the immune response comprising administering to said individual an effective amount of a pharmaceutical comprising the compounds or conjugates, and the salts and solvates thereof as defined herein, particularly as a mucosal pharmaceutical containing an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The compounds or the conjugates or the salts or solvates thereof as defined herein are particular useful as mucosal pharmaceuticals for activating or enhancing in vitro and/or in vivo the antigen presenting function of antigen presenting cells for a therapeutic or prophylactic intervention. That means, the compounds according to the present invention can stimulate macrophages, can stimulate or enhance the humoral immune response, e.g. enhancing or stimulating the production of antibodies. In addition, the compounds can also enhance or stimulate the cellular immune response, e.g. increasing the proliferation of T-cells. In addition, it is possible to use the compounds for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Furthermore, the conjugates according to the present invention are useful for targeting in vitro, ex vivo and/or in vivo cells expressing for example the Toll like receptor system, including but not limited to TLR1, TLR-2 and/or TLR-6 receptor for a prophylactic or therapeutic intervention in the subject. Preferably, the use of the conjugate according to the present invention allows improving the vaccine efficacy by targeting cells expressing the Toll 2 and/or Toll 6 receptor.

Thus, the pharmaceutical composition according to the present invention is preferably a vaccine, comprising said compounds or conjugates, or the salts or solvates thereof as pharmaceutical comprising the adjuvant moiety together with the vaccination component (the antigen moiety) and, optionally, a pharmaceutically acceptable carrier, diluent, preservative, adjuvant other than the adjuvant according to the present invention, immunomodulator or excipient.

The active vaccination component may be any component suitable to elicit, enhance or modulate an immune response in an individual. The active vaccination component is suitable particularly for intranasal, intra-NALT, oral, intra-rectal, conjunctival, intra-vaginal, aerosolized or intra-urethral administration, or administration into the milk ducts of the breast.

The molecules or conjugates according to the present invention and the salts or solvates thereof can be used as active ingredients in pharmaceuticals useful for the prevention or treatment of infectious diseases, septic shock, tumours, autoimmune diseases, allergies, or chronic or acute inflammatory processes. In particular, the compounds or conjugates, or the salts or solvates thereof are contained in pharmaceuticals useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *Helicobacter pylori*, herpes virus, etc.; bacterial infections, such as tuberculosis, leprosy and listeriosis, and parasitic infections such as malaria.

Thus, in a further aspect, the present invention relates to pharmaceutical compositions comprising compounds or conjugates, or the salts or solvates thereof as defined herein, in particular, conjugates containing at least one conjugate moiety as defined herein or salts or solvates thereof and, optionally, a pharmaceutically acceptable carrier. Such pharmaceutical compositions comprise a therapeutically effective amount of the compounds or the conjugates and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral Oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18$^{th}$ ed., Mack Publishing Co., Easton, Pa. (1990)). Such compositions will contain a therapeutically effective amount of the aforementioned conjugates and salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient. The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. "Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in the immunological responses to infection or a suppression of the responses to inflammatory processes or the treatment or prophylaxis of cancer etc.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the conjugates and salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In still another embodiment, the present invention relates to methods of treating individuals suffering from infectious diseases, septic shock, tumours, autoimmune diseases, allergies, or chronic or acute inflammatory processes comprising the step of administering to said individual an effective amount of a pharmaceutical comprising a conjugate or salts or solvates thereof as the active ingredient, and, optionally, a pharmaceutically acceptable carrier. In particular, the method is useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *Helicobacter pylori*, herpes virus, etc.; bacterial infections, such as tuberculosis, leprosy and listeriosis, and parasitic infections such as malaria.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle, preferably bacterial ghosts.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, transcutaneously (topical vaccination), intradermally, intravenously, intra-arterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 µg; however, doses below or above this exemplary range are envisioned, especially considering the aforementioned factors.

In still another aspect, the present invention relates to the use of the compound(s) or conjugate(s), or the salts or solvates thereof as defined herein in a pharmaceutical preparation to control fertility in human or animal populations.

In a further preferred embodiment, the compounds or conjugates are present in at least two different forms in the pharmaceutical composition. according to the present invention. Namely, on the one hand, the pharmaceutical composition according to the present invention contains a first type of conjugate containing antigenic structures of a first component, e.g. of a first virus or a first allergen, and a second type of conjugate containing antigenic structures of a second component, e.g. of a second virus or a second allergen. Alternatively, the compound or the conjugate itself contains the two different antigenic structures of different organisms or species. For example, multi-vaccinating pharmaceuticals can be provided. Since the adjuvant moiety is identical, no problems will arise regarding the use of different adjuvants in the vaccine composition. Thus, in a preferred embodiment, the pharmaceuticals contain at least two different compounds according to the present invention having the same or different adjuvant moiety, preferably the same moiety, different antigenic structures and the same or different conjugate moieties. Alternatively, in a preferred embodiment, the compound or the conjugate according to the present invention contains an adjuvant moiety, two antigenic moieties of different sources, i.e. not from the same species or not from the same organism, and, optionally, a conjugate moiety.

Further, depending on the use of the compounds according to the present invention, the pharmaceutical composition may be in form of liquid or solid preparations and may be for immediate or sustained-release.

These and other embodiments are disclosed and encompassed by the claims and the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.qov/PubMed/medline.html. Further databases and addresses, such as http://www.ncbi.nlm.nih.gov/, http://www.infobiogen.fr/, http://www.tigr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

The present invention will be described by the Examples below without limiting the same thereto.

EXAMPLES

Example 1

Preparation of BPPcysOVA'''PEG

Peptide synthesis resin TentaGel S RAM (Rapp Polymere, Tübingen, Germany) (100 µmol) was Fmoc-deprotected with 20% piperidin in DMF, washed with DMF and treated with Fmoc-NH-(PEG)27-COOH (Novabiochem/Merck, Nottingham, UK) (463.4 mg, 300 µmol), TBTU (96.3 mg, 300 µmol) and diisopropylethyl amine (105 µl, 600 µmol) in DMF for 18 h [1]. The ova-specific peptide sequences ISQAVHAAHAEINEAGRAA (MHC cl. II)-AA (linker)-SIINFEKL (MHC cl. I) (Seq. ID. No. 1) were assembled on the solid support with a Pioneer automatic peptide synthesizer (Applied Biosystems) employing Fmoc chemistry with TBTU/diisopropylethyl amine activation. Side chain protections were as follows: Glu and Ser: t-Bu; Asn, Gln and His: Trt; Arg: Pbf; Lys: Boc. Double couplings of 1 h each were employed throughout the synthesis. After final Fmoc-deprotection and washing with DMF and DCM a test cleavage with 10 mg of the product was carried out by a 3 hour treatment with TFA containing 3% triisopropylsilane and 2% water (1 ml). An HPLC- and MALDI analysis of the crude product revealed a satisfying quality with the major product showing the expected molecular mass. BPPcys (Fmoc-protected S-(2(/R/),3-bis(palmitoyloxy)propylR-cystein) (125.7 mg, 150 µmol), TBTU (48 mg, 150 µmol): and di-isopropylethyl amine (53 µl, 300 µmol) in DMF were added to the solid support. After an incubation of 18 h the resin was washed with DMF followed by DCM. Cleavage from the support and side chain deprotection was carried out by a 5 hour treatment with TFA containing 3% triisopropylsilane and 2% water (10 ml). After removing the resin by filtration and evaporation of most of the TFA, the crude product was precipitated with t-butylmethyl ether. The peptide was purified by preparative HPLC (RP-18) with water/acetonitrile gradients containing 0.1% TFA and characterized by MALDI-MS.

Example 2

In Vitro Stimulation of Primary Bone Marrow-Derived Murine Dendritic Cells with BPPcysOva'''PEG.

Experimental protocol: primary bone marrow-derived dendritic cell cultures were obtained from BALB/c mice following in vitro maturation of precursors in the presence of recombinant GM-CSF ($5 \times 10^4$ U/ml), according to established protocols. Mature dendritic cells were stimulated with 10 ng/ml of *E. coli* lypo-polysaccharide (LPS) or 5 ng/ml of BPPcysOva'''PEG, after 12, 24 and/or 48 h stimulation cells were analyzed by flow cytometry to assess the expression of surface markers which are relevant for their antigen presentation capacity.

In order to identify compounds which may have potential as active pharmaceuticals combining adjvant activity and immunogenic activity for in vivo applications in the vaccinology field, a first in vitro screening based on the use of primary cultures of bone marrow-derived dendritic cells was established. Dendritic cells were selected since they represent the most efficient antigen presenting cells and they play a key role by primary immune responses. In fact, they are the only cell type able to activate resting T cells initiating primary immune responses in vivo. Thus, dendritic cell cultures were treated with the tested moieties or Ova protein or Ova peptides. At different time intervals, samples were taken, stained with fluorescent-labeled antibodies specific for cellular markers critical for the antigen presenting capacities of dendritic cells, and analyzed by flow cytometry. The obtained results demonstrated that in contrast to the control, the expression of the adhesion molecule ICAM-1 (CD54) was up-regulated in BPPcysOva'''PEG-treated dendritic cells.

Example 3

In Vitro Proliferation of Antigen Specific Spleen and Lymph Node Cells with BPPcysOva'''PEG Experimental protocol: Spleens and lymph nodes from C57BL6 OT-I and OT-II mice were removed and pooled for analysis of cellular immune responses. Lymph node and spleen cell suspensions were labeled with CFSE (Invitrogen) and adjusted to $5 \times 10^6$ cells/ml in complete medium. Then, cells were seeded with 100 µl per well in a flat-bottomed 96-well microtiter plate (Nunc) and plates were incubated for 5 days in the presence or absence of different concentrations (0.1, 1 and 10 µg/ml) of BPPcysOva'''PEG. Each concentration was tested in triplicates.

Figure 3:
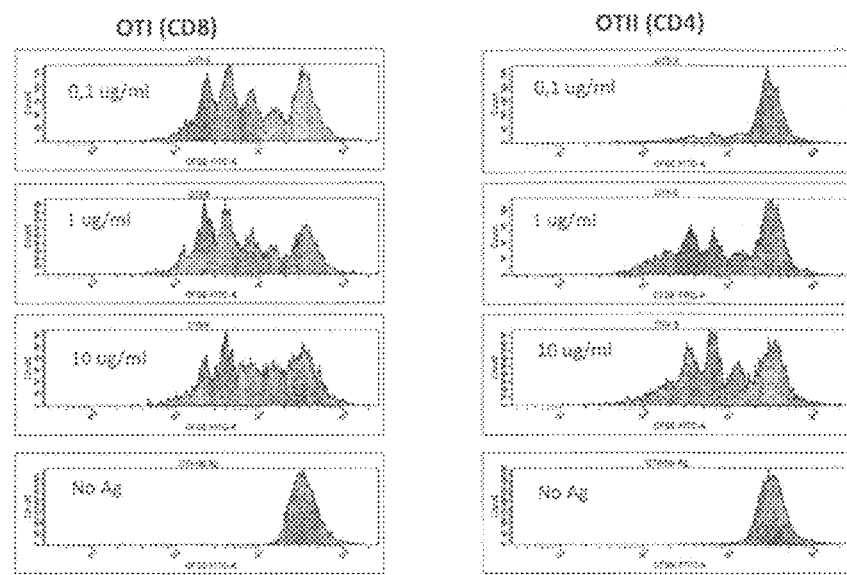

T cell-mediated immune responses were investigated 96 h by measuring the proliferation of cells recovered from spleens after restimulation with BPPcysOva'''PEG. Non-Ag restimulated spleen cells were chosen as negative controls (FIG. 3). The administration of BPPcysOva'''PEG triggered the induction of an efficient proliferative response of spleen cells shown by the loss of CFSE expression. Taking into consideration that the BPPcysOva'''PEG has a promising effect on DC activation and maturation, next the capacity of these APC to stimulate the proliferation of antigen-specific CD8+ and CD4+ T cells was evaluated. Concentrations below $10^{-8}$ M of BPPcysOva'''PEG were still able to induce an antigen specific proliferation of CD4+ T cells shown by the reduction of CFSE+ cells (FIGS. 4A-E). DC stimulated with BPPcysOva'''PEG or with the CD4 peptide alone was able to stimulate very efficiently the proliferation of co-incubated Ova-specific CD4+CD25+Foxp3+ regulatory T cells, which were derived from OTII mice, whereas only weak stimulation of CD8+ T cells was observed (FIG. 4C+E). DC stimulated with Ova alone or co-administered with BPPcysMPEG were able to stimulate very efficiently the proliferation of co-incubated Ova-specific CD8+ T cells, whereas only weak stimulation of CD4+ T cells was observed (FIG. 4B+D).

Example 4

BPPcysOva'''PEG Stimulates In Vitro Efficient T Cell-Mediated Proliferative Responses Experimental protocol: Spleens were removed and pooled for analysis of cellular immune responses. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble Ova. Each concentration was tested in triplicates. During the final 18 h of culture, 1 µCi of [$^3$H]thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [$^3$H]thymidine into the DNA of proliferating cells was determined by a β-scintillation counter (Wallac 1450, Micro-Trilux). The results are expressed as the arithmetic mean of [$^3$H]thymidine uptake in cpm.

T cell-mediated immune responses were investigated after 96 h by measuring the proliferation of cells recovered from spleens after restimulation with BPPcysOva'''PEG. Ova protein or Ova specific CD4 and CD8 peptides restimulated spleen cells were chosen as negative controls. The administration of BPPcysOva'''PEG as well as Ova co-administered with BPPcysMPEG or MALP-2 triggered the induction of an efficient proliferative response at systemic (spleen cells) levels with high stimulation index SI>4 even at very low concentrations of 0.001 µg/ml. In opposite, Ova protein or Ova specific CD4 and CD8 peptides restimulated spleen cells showed no proliferation at all (SI<1.5).

Example 5

BPPcysOva'''PEG Stimulates Efficient T Cell-Mediated Proliferative Responses

Experimental protocol: Spleens were removed and pooled for analysis of cellular immune responses. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of Ova. Each concentration was tested in triplicates. During the final 18 h of culture, 1 μCi of [³H]thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [³H]thymidine into the DNA of proliferating cells was determined by a β-scintillation counter (Wallac 1450, Micro-Trilux). The results are expressed as the arithmetic mean of [³H]thymidine uptake in cpm.

T cell-mediated immune responses were investigated at day 42 by measuring the proliferation of cells recovered from spleens after in vitro restimulation with Ova. Thus, mice were immunized with either Ova alone, Ova co-administered with 5 μg BPPcysMPEG or immunized with 5 or 10 μg of BPPcysOva′′′PEG alone. On day 42 following vaccination, spleens cells were purified, re-stimulated in vitro in the presence of enhanced concentrations 0.1 up to 40 μg/ml of Ova and their proliferative capacity was estimated by measuring the incorporation of [³H]thymidine using a β-scintillation counter. Spleen cells from animals immunized by s.c. injection of Ova alone, which were chosen as a positive control, exhibited a significant proliferative response as compared to the non immunized group. A further increase in proliferation was noted in spleen cells from animals with antigen co-administrated with BPPcysMPEG. Of note, a strong T cell proliferative response was also observed with spleen cells of mice immunized with BPPcysOva′′′PEG alone by both routes. While i.n. administration of LPS free Ova alone failed to induce detectable cellular proliferation, administration of BPPcysOva′′′PEG triggered the induction of an efficient proliferative response at systemic (spleen cells) levels, shown by the increased stimulation index. The use of BPPcysOva′′′PEG (5 or 10 μg) resulted in an increment of the T cell proliferation.

Example 6

Nitrogen Monoxide Release Assay

Experimental protocol: In brief, peritoneal macrophages from C3H/HeJ mice were used as the macrophage source. They were cultured in 96-well microtiter plates and stimulated simultaneously with rIFN-γ and a serial dilution of macrophage activator. Insofar as necessary, the macrophage activators were dissolved in 25 mM octylglucoside in the first dilution step and then diluted further with medium (i.e. R-Malp-2). After an incubating time of 45-48 hours, the nitrate was reduced with nitrate reductase and the starting substance nitrogen monoxide was determined, as the sum of nitrate and nitrite, using Griess' reagent. 1 unit (U)/ml is defined as the dilution at which half-maximal stimulation takes place.

Figure 2:
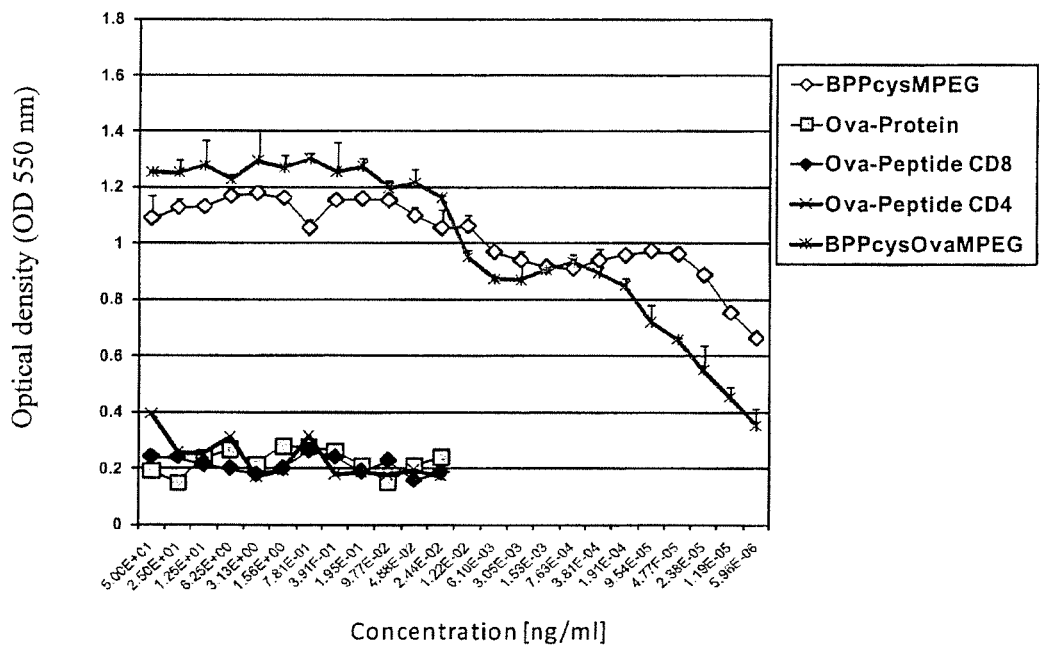
Figure 4:
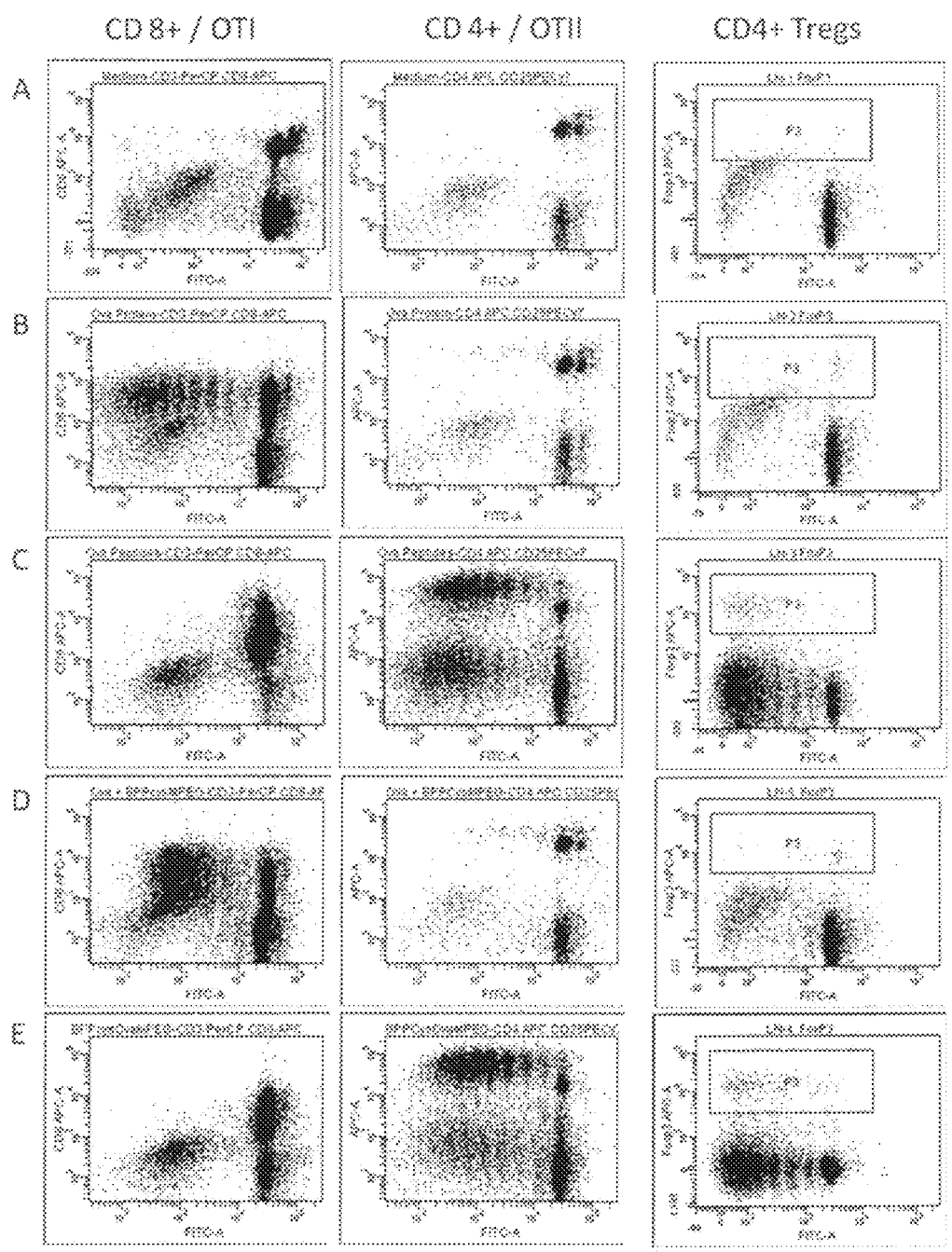

The results of the macrophage activation test are shown in FIG. 4. BPPcysOva′′′PEG i.e. a macrophage activator according to this invention has a comparable potential for activating macrophages than has the known BPPcysMPEG, whereas the protein, or the CD4 and CD8 peptides showed no potency to activate the NO secretion of macrophages (FIG. 2). The figure shows that the activation effect in the case of BPPcysOva′′′PEG is not noticeably improved by adding a solubilizer, in this case octylglucoside, whereas such an addition is required for the effect of R-Malp-2 to be displayed optimally. The novel BPPcysOva′′′PEG conjugate according to this invention does not, therefore, require any additional, and possibly physiologically disadvantageous, solubilization by means of an organic solvent or detergent.

Example 7

Intranasal Administration of BPPcysOva′′′PEG Stimulates Efficient Systemic Humoral Responses Experimental protocol 1: six-eight weeks-old female C57BL6 mice were purchased from Harlan Winkelmann GmbH (Borchen, Germany) and treated in accordance with local and European Community guidelines. Groups of 5 mice each were immunized on day 1, 14 and 28 with 30 μg of Ova (Sigma Chemie, Deisenhofen, Germany) or LPS-free Ova (EndoGrade Ovalbumin, Hyglos GmbH) alone, co-administered with 5 μg of BPPcysMPEG or with 5 to 10 μg of synthetic BPPcysOva′′′PEG alone. For intranasal (i.n.) immunization, 10 μl were applied to each naris, whereas for the s.c. the compounds were resuspended in 50 μl of PBS per dose. Serum samples were collected at different time points (day 0, 13, 27 and 38) after immunization and stored at −20° C. prior to determination of Ova-specific antibodies. 96-well Nunc-Immuno MaxiSorp assay plates (Nunc, Roskilde, Denmark) were coated with 100 μl of Ova (Sigma Chemie, Deisenhofen, Germany) at 5 μg/ml in 0.05 M carbonate buffer (pH 8.2) per well. Serial two-fold dilutions of sera or lavages in PBS with 1% BSA and 0.05% Tween 20 were added (100 μl/well), and plates incubated for 2 h at 37° C. After washing, biotinylated γ-chain-specific goat anti-mouse IgG (Sigma Chemie, Deisenhofen, Germany) was added, and plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. Endpoint titers were expressed as the reciprocal $\log_2$ of the last dilution, which gave an optical density at 405 nm of 0.1 units above the values of the negative controls after 15 to 30 min of incubation.

Experimental protocol 2: Isotyp ELISA: 96-well Nunc-Immuno MaxiSorp assay plates (Nunc, Roskilde, Denmark) were coated with 100 μl of Ova (Sigma Chemie, Deisenhofen, Germany) at 5 μg/ml in 0.05 M carbonate buffer (pH 8.2) per well. Serial two-fold dilutions of sera or lavages in PBS with 1% BSA and 0.05% Tween 20 were added (100 μl/well), and plates incubated for 2 h at 37° C. After washing, biotin-conjugated rat anti-mouse IgG1, IgG2a, IgG2b, or IgG3 (Pharmingen, Hamburg, Germany) were added to determine IgG subclasses. Plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. To determine the concentration of IgG subclasses in serum, standard curves were obtained by coating the wells with an isotype-specific goat anti-mouse IgG, and then by incubating with purified mouse IgG1 and IgG2c antibodies (Dianova, Hamburg, Germany).

Figure 5A:
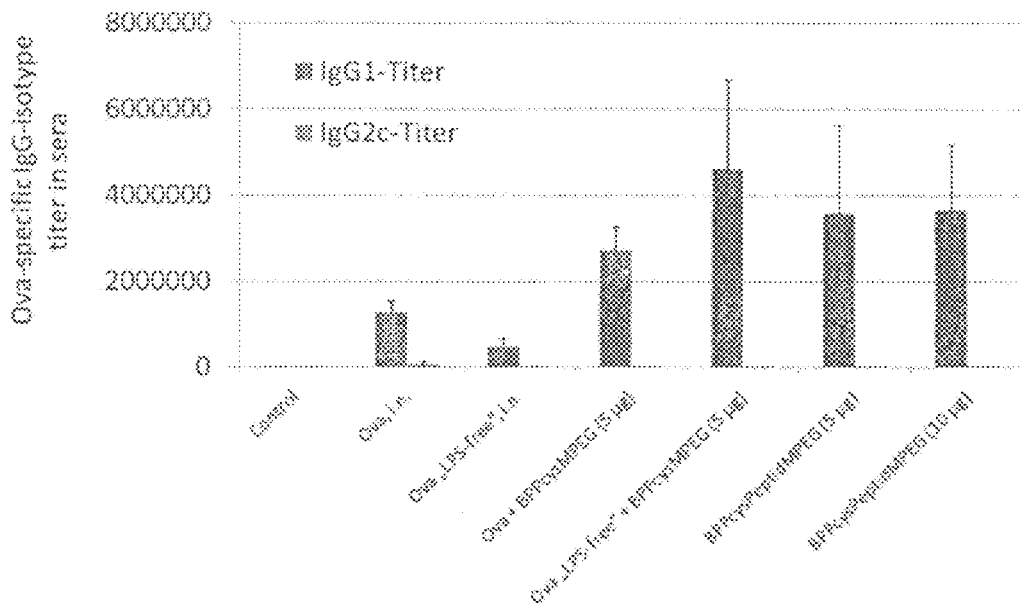

To analyze in detail the immune responses stimulated using BPPcysOva′′′PEG by the two most effective routes, namely s.c. and i.n., and compare it with a well-established mucosal adjuvant, such as the parenteral compound BPPcysMPEG, the capacity of BPPcysOva′′′PEG to stimulate efficient humoral immune responses was evaluated, by determining the serum titers of Ova-specific IgG1 antibodies in vaccinated mice. As shown in FIG. 5A, i.n. administration of Ova alone (30 μg/dose) resulted in the induction of lower antibody titers (endpoint titer: up $10^6$). In contrast, in the presence of BPPcysOva'''PEG alone, i.n. administration induced higher titers of specific IgG1 in all mice already after one dose, and by the end of the immunization protocol, titers were higher than $3.6 \times 10^6$ (FIG. 5A). The kinetics and the overall efficacy of the antibody responses obtained using 5 μg of BPPcysOva'''PEG per dose were similar to those observed by administering 10 μg or Ova co-administered with BPPcysMPEG.

Figure 6:
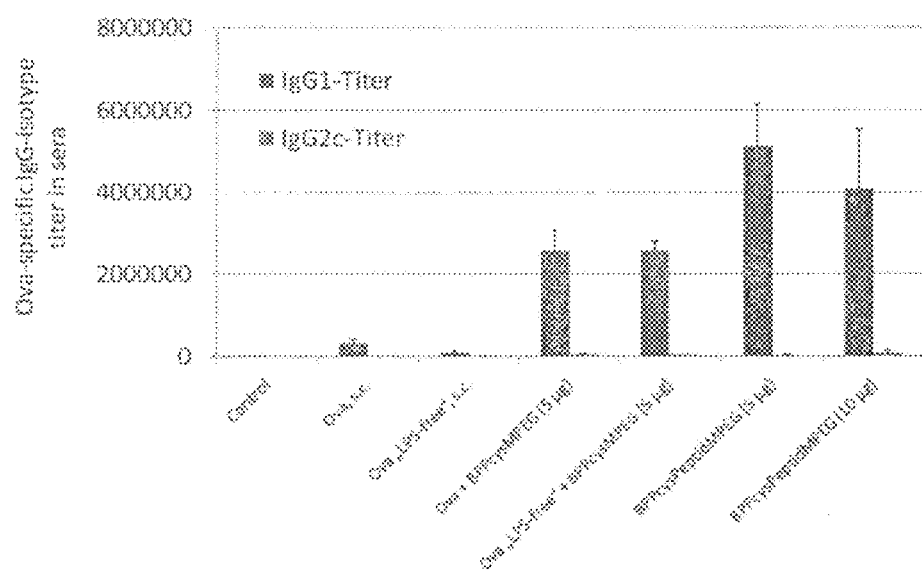

A significant adjuvanticity in combination with eliciting an immune response was also observed when BPPcysOva'''PEG was administered by the s.c. route. Specifically, s.c. injection of BPPcysOva'''PEG resulted in increased Ova-specific IgG1 isotype titers in comparison to animals immunized with Ova alone or co-administered with BPPcysMPEG (FIG. 6).

Example 8

Intranasal Administration of BPPcysOva'''PEG Stimulates Efficient Local Antibody Responses Experimental protocol: at day 38, mice were sacrificed and the final sampling was performed. Vaginal and lung lavages were obtained by flushing the organs with 1 ml of PBS supplemented with 50 mM EDTA, 0.1% BSA, and 10 mM PMSF. Lavages were then centrifuged to remove debris (10 min at 3000×g), and supernatant fluids were stored at −20° C. To determine the concentration of total IgA present in the lung and vaginal lavages, serial dilutions of the corresponding samples were incubated in microtiter plates that were previously coated with goat anti-mouse IgA (Sigma Chemie), as capture antibodies (100 μl/well). Serial dilutions of purified mouse IgA (Sigma Chemie) were used to generate a standard curve.

Figure 5B:
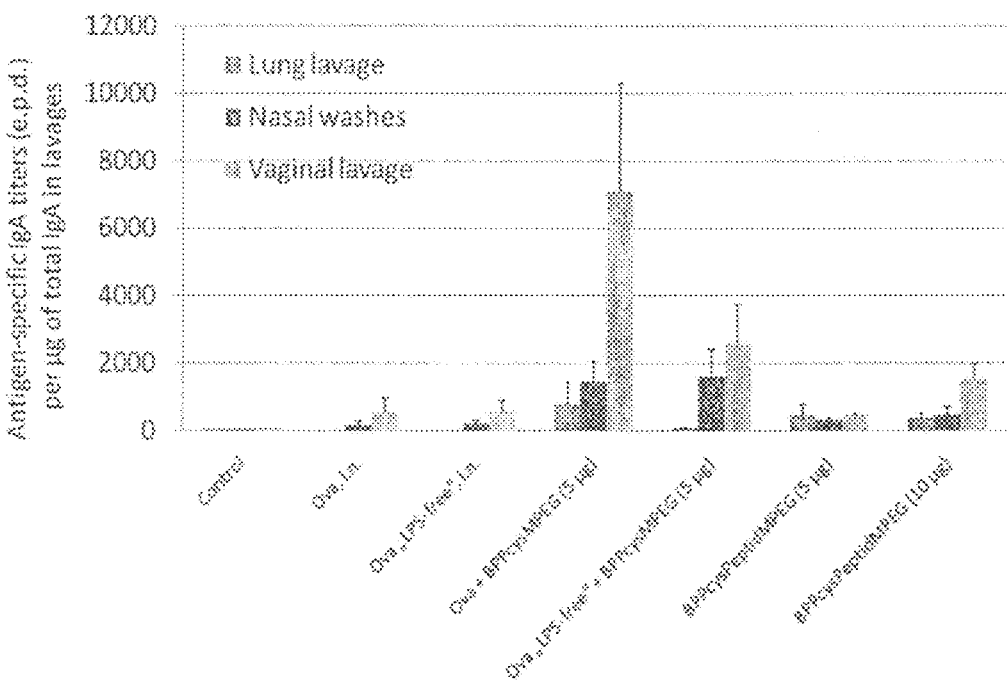

To investigate the capacity of BPPcysOva'''PEG to stimulate local immune responses given by the i.n. route, we analyzed the production of Ova-specific secretory IgA in lung, nasal and vaginal lavages from immunized animals. While i.n. immunization with Ova alone failed to stimulate the production of detectable levels of Ova-specific IgA in lung lavages, a significant increase in the levels of antigen-specific IgA was detected in animals immunized with Ova co-administered with BPPcysMPEG or BPPcysOva'''PEG alone (FIG. 5B). The administration of BPPcysOva'''PEG resulted in the stimulation of efficient IgA production also at distant mucosal sites, as demonstrated by the presence of significant concentrations of Ova-specific IgA in vaginal lavages (FIG. 5B). No statistically significant differences were observed in the levels of mucosal Ova-specific antibodies between animals immunized with 5 μg or 10 μg of BPPcysOva'''PEG. However, strongest responses were more pronounced following the administration with Ova co-administered with BPPcysMPEG.

Example 9

Analysis of the T Helper Patterns Stimulated by Using BPPcysOva'''PEG

Experimental protocol: Cytometric Bead Array: Culture supernatants from proliferating cells were collected on days 2 and 4, and stored at −70° C. Determinations of GM-CSF, IFN-gamma, IL-1alpha, IL-2, IL-4, IL-5, IL-6, IL-10, IL-17 and TNF-alpha were performed by cytometric bead array analysis using the commercial kit from Bender, according to the manufacturer's instructions. A standard curve was generated for each cytokine by using the corresponding recombinant murine cytokines (Pharmingen). Probes were incubated at room temperature for additional 2 h. The probes were then analyzed by flow cytometry as described by the protocol of Bender.

Figure 8A:
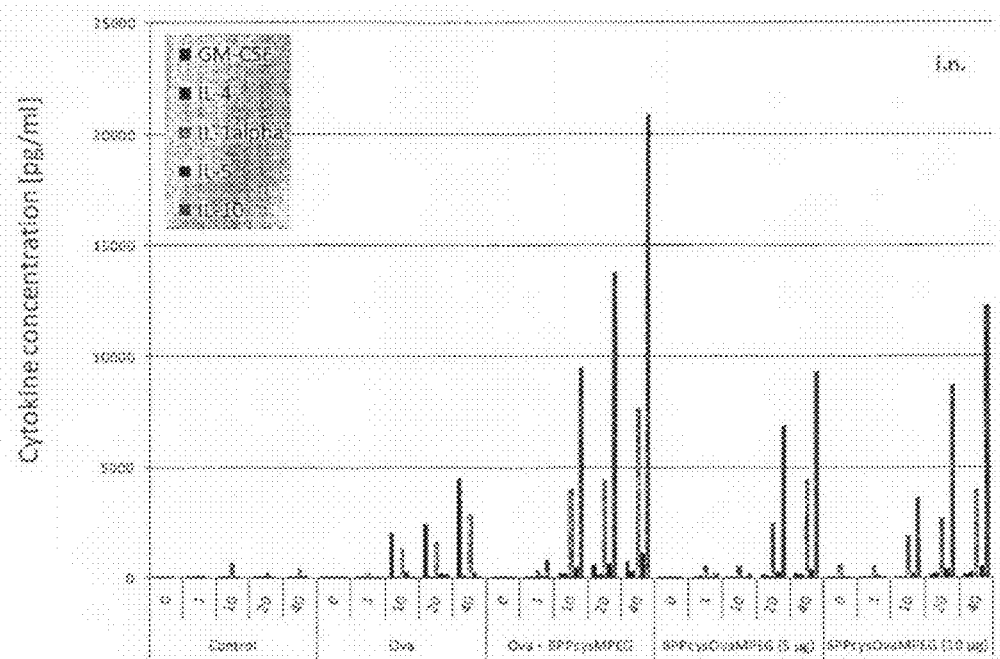
Figure 8B:
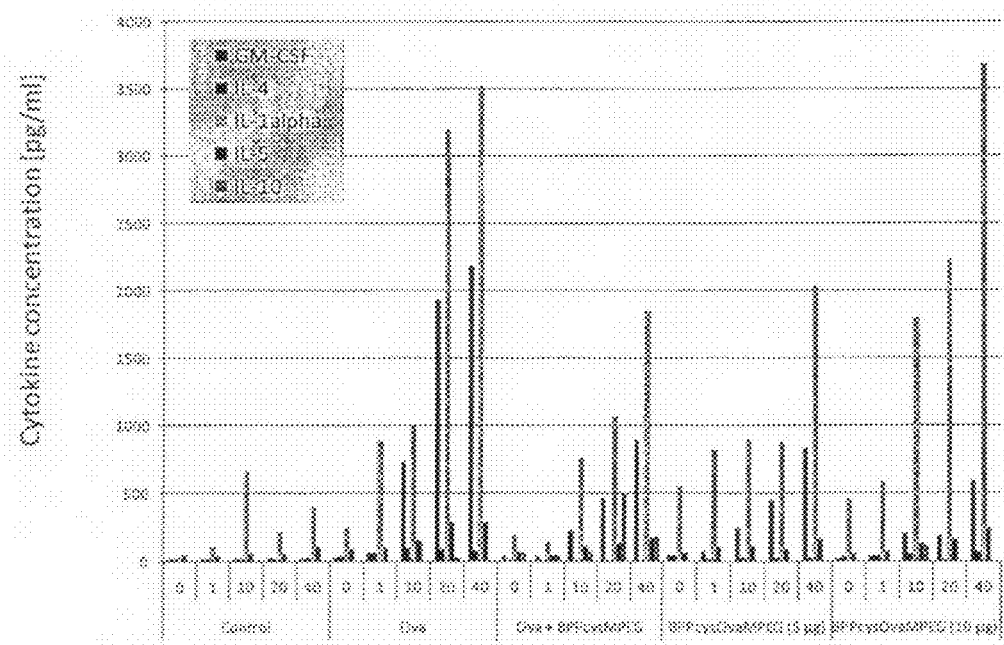

To characterize the type of Th response stimulated following immunization, the content of GM-CSF, IFN-gamma, IL-1alpha, IL-2, IL-4, IL-5, IL-6, IL-10, IL-17 and TNF-alpha was measured in supernatants from in vitro re-stimulated spleen cells (FIG. 8). Among these cytokines, GM-CSF, IL-4 IL-1alpha, IL-5 and IL-10 were found to be the most prominent, suggesting that a dominant Th2 response pattern was stimulated. The levels of GM-CSF, IL-4 IL-1alpha, IL-5 and IL-10 were higher in mice vaccinated with BPPcysOva'''PEG by i.n. route. In fact, the strong stimulation of GM-CSF, IL-4 IL-1alpha, IL-5 and IL-10 secretion is congruent with the role played by this cytokine in the inhibition of cytokine synthesis by Th1 cells, the enhancement of B cells proliferation and the stimulation of IgA production. Interestingly, although minor secretion of Th1-cytokines IL-2 and IFN-γ was also stimulated in cells from mice vaccinated with Ova and BPPcysOva'''PEG by the i.n. route. These results confirm that, although Th2 type responses are prevalent, BPPcysOva'''PEG also helps to stimulate Th1 cells.

Example 10

Analysis of the T Helper Patterns Stimulated by Using BPPcysOva'''PEG by Elispot Experimental protocol: Spleens were removed and pooled for analysis of cellular immune responses. Cells were grown in RPMI 1640 supplemented with 10% fetal calf serum, 100 U/ml of penicillin, 50 μg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 μl per well in a flat-bottomed 96-well microtiter plate (Nunc) and plates were incubated for 4 days in the presence of different concentrations of soluble Ova. Each concentration was tested in triplicates.

Figure 7A:
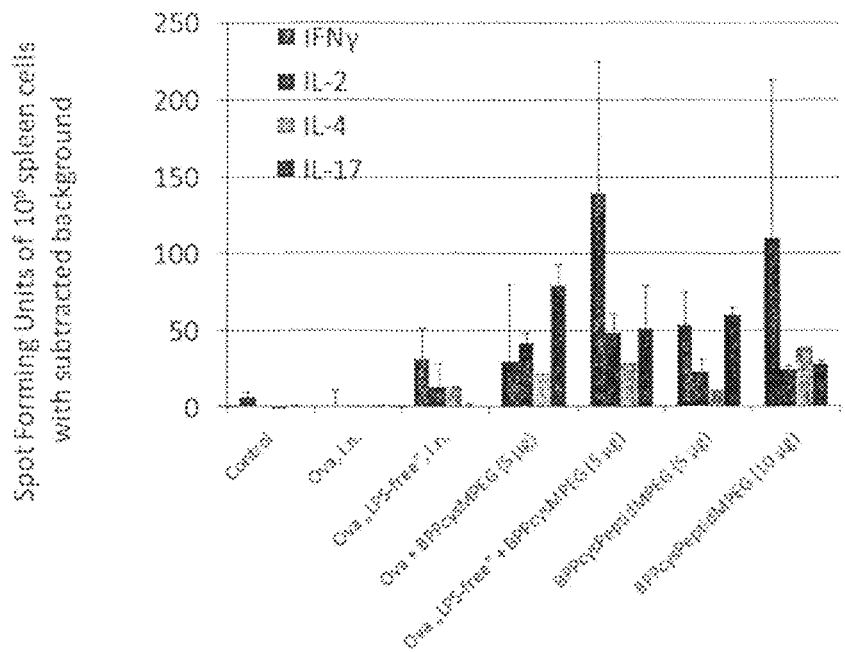

An increment in the number of splenic IFNγ producing cells was observed in animals immunized with Ova co-administered with BPPcysMPEG or BPPcysOva'''PEG alone, in response to restimulation with a peptide encompassing the MHC class I-restricted immunodominant epitope from Ova (CD8 epitope) after vaccination by both routes (FIG. 7A/B). In contrast, INFg producing cells were narrowly detectable after i.n. administration of Ova. However, i.n. vaccination of Ova with additional adjuvant BPPcysMPEG resulted in amounts of IFNγ expressing cells similar to the level determined after s.c. vaccination with BPPcysOva'''PEG, whereas the co-administration of Ova alone or co-administered with BPPcysMPEG showed a reduction in INFg producing cells. Furthermore, a strong expression of splenic IL-2 and IL-4 producing cells after restimulation with the β-Gal protein was shown in mice immunized with Ova co-administered with BPPcysMPEG or BPPcysOva'''PEG alone by the i.n. route.

Example 11

Analysis of the Cytotoxic T Cell Response Stimulated by Using BPPcysOva'''PEG

Experimental protocol: Antigenic epitopes delivered by linking to BPPcysMPEG induce superior CTL response.

Mice (n=3) were immunized with BPPcysOVA'''PEG (10 μg/mouse) or with OVA (3 mg/mouse) co-administered with BPPcysMPEG(3 μg/mouse) or with OVA257-264 (10 μg)+ OVA323-339 (10 μg) co-administered with BPPcysMPEG (10 μg/mouse), by giving foot pad injection in two doses at an interval of one week. The CTL response in these mice was compared in an in vivo cytotoxicity assay. The data is represented as mean and SEM of percentage specific lysis of target cells obtained from each group. The result is representative of two independent experiments.

Figure 9:
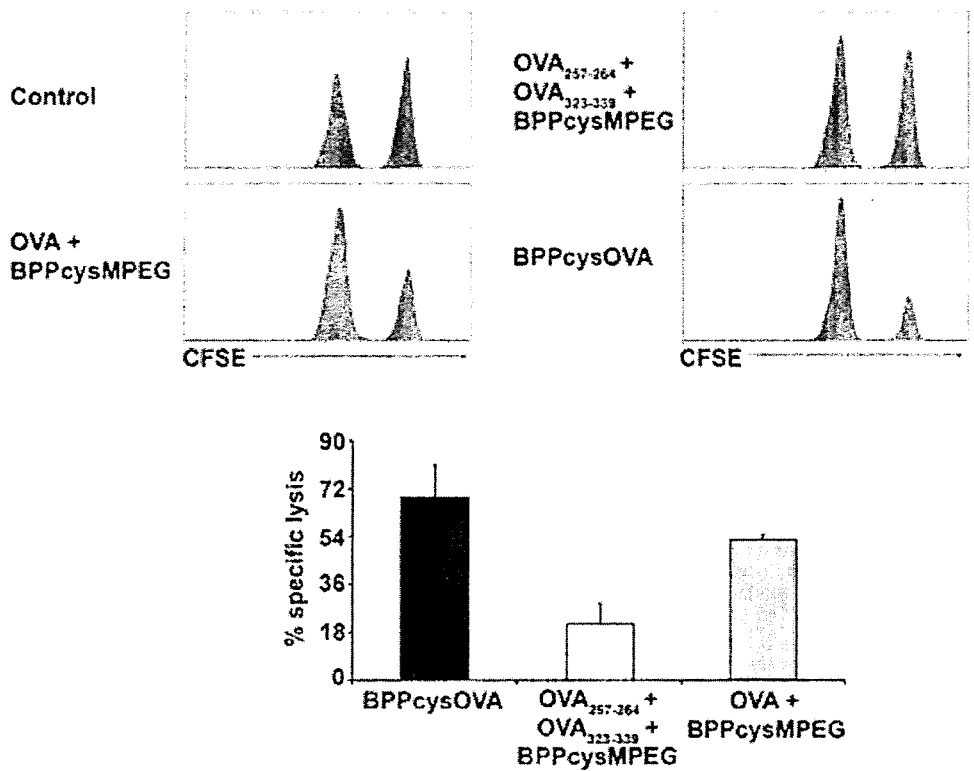
Figure 10A:
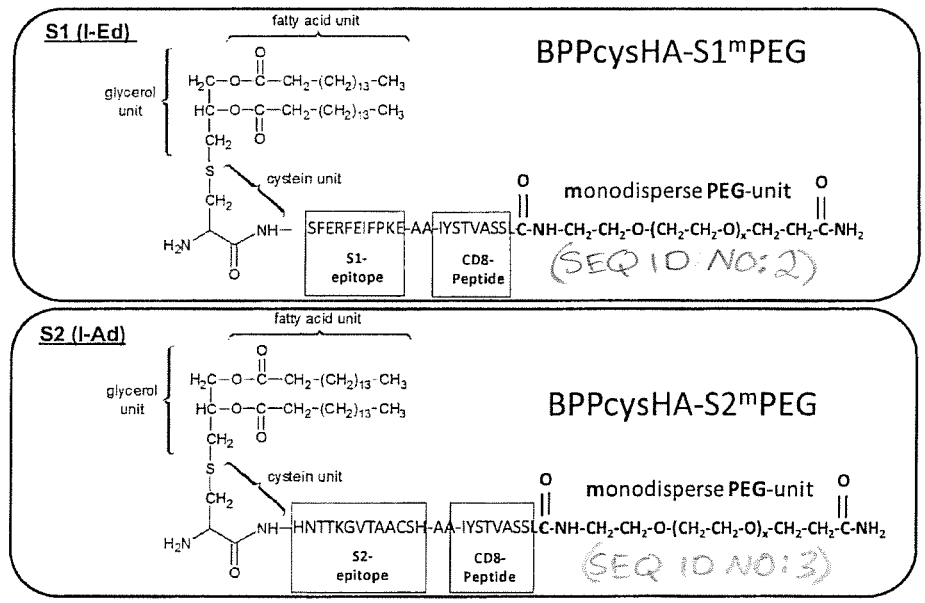

The effective delivery of antigens which were directly linked to an adjuvant in inducing CTL responses was analyzed with a MALP-2 derivative chemically linked to Ova antigenic epitopes. Thereby, the CD8 $OVA_{257-264}$ and CD4 $OVA_{323-339}$ peptides were chemically linked to a MALP-2 derivative and MPEG to enhance the stability and solubility. This compound was termed as BPPcysOva'''PEG. Mice were immunized with BPPcysOva'''PEG through foot pad injections in two doses at an interval of one week. Five days post first boost mice were systemically challenged with OVA-peptide-pulsed target cells and the specific lysis of these target cells was determined in the draining lymph node. Interestingly, effective CTL-mediated cytotoxicity was observed only in mice which were immunized with BPPcysOva'''PEG. In opposite to this, only a weak CTL activity was observed when mice were immunized with similar amounts of $OVA_{257-264}$ and CD4 $OVA_{323-339}$ peptides co-administered with BPPcysMPEG. Furthermore, mice which were immunized with OVA protein co-administered with BPPcysMPEG showed also weaker CTL activity (FIG. 9).

These results support the fact that antigens linked to TLR agonists induce stronger immune responses in comparison to co-administration of antigens (both peptides and/or protein) and adjuvants.

Results

Initial in vitro screening studies were performed in order to characterize the potential of BPPcysOva'''PEG and other tested molecules as activators of antigen presenting cells. As targets bone-marrow derived dendritic cells, which were obtained by precursors treated with GM-CSF have been used. In fact, dendritic cells plays a central role in primary immune responses, being (i) the most efficient antigen-presenting cells, (ii) the major source of epitopes for specific T-cell clones, (iii) the main activators of resting T cells, which are able to initiate primary immune responses in vivo. BPPcysOva'''PEG exhibit a strong activity on primary dendritic cells shown by the strong stimulation of Ova-specific CD4+ T cells (FIG. 4).

Furthermore, the novel compound BPPcysPeptide'''PEG is still able to activate peritoneal C3H macrophages shown by the release of nitric oxide after incubation as good as the parenteral compound BPPcysMPEG, whereas the protein, or the CD4 and CD8 Ova peptides showed no potency to activate the NO secretion of macrophages demonstrating the adjuvant activity (FIG. 2). T cell-mediated immune responses were investigated 96 h by measuring the proliferation of cells recovered from spleens after restimulation with BPPcysOva'''PEG. Non-Ag restimulated spleen cells were chosen as negative controls (FIG. 3).

In vivo studies showed that when co-administered with a model antigen (Ovalbumin) by either the intranasal (i.n.) or subcutanous (s.c.) route. The immunization of C57BL6 mice with Ova alone or co-administered with BPPcysMPEG or immunization with BPPcysOva'''PEG alone showed no adverse effect during the immunization period. A dose of 5 to 10 μg BPPcysOva'''PEG was capable of increasing Ova-specific serum IgG titers. By using this novel compound, almost maximal IgG1 isotype responses were already stimulated using 5 μg per dose (FIGS. 5A and 6). The mucosal immune system was also effectively stimulated when BPPcysOva'''PEG was administered by the i.n. route. This demonstrates that BPPcysOva'''PEG is not only able to stimulate local mucosal immune responses, but that there is also a homing of cells to other distant mucosal territories, leading to efficient mucosal immune responses (FIG. 5B). This is a property which can be observed using a few of the available mucosal delivery systems/tools only. As demonstrated in FIGS. 5 and 6, the IgG-isotype titer was remarkably increased when using BPPcysOva'''PEG. The effect of BPPcysOva'''PEG as an adjuvant was independent of the route of administration. For BPPcysOva'''PEG the results confirm that a Th2 response was induced in mice. The results show that not only antigen-specific IFNg and IL-2 secreting cells, but also IL-4 secreting cells were increased in number in mice receiving BPPcysOva'''PEG by the i.n. route, whereas enhanced antigen-specific IFNg and IL-2 secreting cells were induced, when BPPcysOva'''PEG was given by the s.c. route (FIG. 7A/B). GM-CSF, IL-4 IL-1 alpha, IL-5 and IL-10 were found to be the most prominent, suggesting that a dominant Th2 response pattern was stimulated. The levels of GM-CSF, IL-4 IL-1 alpha, IL-5 and IL-10 were higher in mice vaccinated with BPPcysOva'''PEG by i.n. route. In fact, the strong stimulation of GM-CSF, IL-4 IL-1 alpha, IL-5 and IL-10 secretion is congruent with the role played by this cytokine in the inhibition of cytokine synthesis by Th1 cells, the enhancement of B cells proliferation and the stimulation of IgA production (FIG. 8). The administration of BPPcysOva'''PEG stimulated cellular immune responses in spleen. Altogether, our results demonstrated that in contrast to what expected, the synthetic BPPcysOva'''PEG represents a new efficient adjuvant for the mucosal delivery of peptide antigens. It is important to highlight that the low concentration of 5 μg of BPPcysOva'''PEG induce the same proliferation when compared with 30 μg of the Ova protein. Effective CTL-mediated cytotoxicity was observed only in mice which were immunized with BPPcysOva'''PEG. In opposite to this, only a weak CTL activity was observed when mice were immunized with similar amounts of $OVA_{257-264}$ and CD4 $OVA_{323-339}$ peptides co-administered with BPPcysMPEG (FIG. 9).

FIGURES

FIG. 1: (A) Structural formula of BPPcysOva'''PEG. The molecule exhibits a molecular weight of 4818 Da.

FIG. 2: Nitrogen monoxide release assay. Peritoneal macrophages from C3H/HeJ mice were used as the macrophage source. They were cultured in 96-well microtiter plates and stimulated simultaneously with rIFN-γ and a serial dilution of macrophage activator. After an incubating time of 45-48 hours, the nitrate was reduced with nitrate reductase and the starting substance nitrogen monoxide was determined, as the sum of nitrate and nitrite, using Griess' reagent.

FIG. 3: In vitro proliferation studies using spleen and lymph node cells. Cells were obtained from C57BL6 OT I and OT II mice and labeled with CFSE. The CFSE positive spleenocytes and/or lymph node derived cells were stimulated with 0.1, 1 or 10 μg/ml of BPPcysOva'''PEG and analyzed after 96 h incubation by flow cytometry.

FIG. 4: Proliferation of CD8+, CD4+ and regulatory T cells. DC were generated from bone marrow of C57BL/6 mice and incubated with 10 μg/mL of B) Ova C) Ova peptides, D) Ova in the presence of BPPcysMPEG and E)

BPPcysOva′′′PEG alone (A) Control) for 24 h. The following day, CD4+ T cells from spleens of OT2-tg animals or CD8+ T cells of OT1-tg animals were isolated. After staining with CFSE, CD8+, CD4+ T cells were co-cultured with adjuvant-treated DCs for 4 days. The decrease of CFSE-FITC expression due to cell division of CD8+ or CD4+ T cells were analysed by flow cytometric analysis. One representative experiment out of two is shown.

FIG. 5: Humoral responses stimulated following vaccination using BPPcysOva′′′PEG. Mice were immunised (A) by intranasal route with either ovalbumin (30 μg) alone or mixed with BPPcysMPEG (5 μg) or BPPcysOva′′′-PEG (5 or 10 μg) alone on days 0, 14 and 28. At day 38 post primary immunisation, serum samples were collected and the IgG 1 and IgG2c titres of Ova-specific antibodies were determined by ELISA. (B) Local humoral responses stimulated following vaccination using BPPcysOva′′′PEG as adjuvant. At day 38 post primary immunisation broncho alveolar lavage (BAL), nasal lavages (NL) and Vaginal lavages (VL) were collected and the Ova-specific secretory IgA (sIgA) expression in samples of immunized mice were determined by ELISA.

FIG. 6: Humoral responses stimulated following vaccination using BPPcysOva′′′PEG. Mice were immunised by subcutaneous routes with either ovalbumin (30 μg) alone or mixed with BPPcysMPEG (5 μg) or BPPcysOva′′′- PEG (5 or 10 μg) on days 0, 14 and 28. At day 38 post primary immunisation, serum samples were collected and the IgG 1 and IgG2c titres of Ova-specific antibodies were determined by ELISA.

Figure 7B:
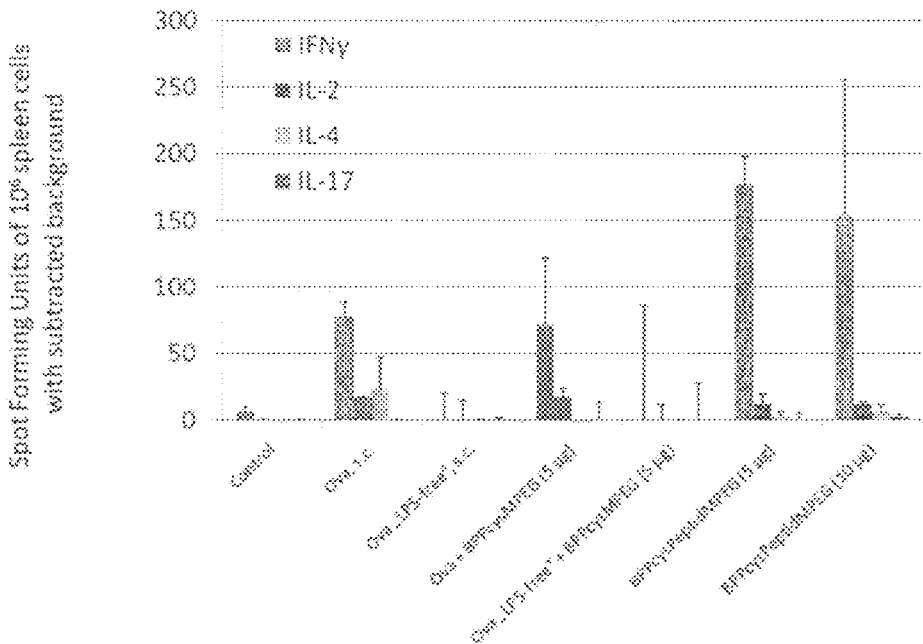

FIG. 7: Detection of IFNgamma, IL-2, IL-4 and IL-17-secreting cells in immunized mice. Spleen cells ($1\times10^6$ and $5\times10^5$ cells/well) recovered from animals vaccinated by the (A) i.n. or (B) s.c. route were incubated in the presence of either the Ova protein (for IL2 and IL4) or a Ova peptide (TPHPARIGL) encompassing its immunodominant MHC class I-restricted epitope (for IFNgamma). Then, the numbers of IFNgamma, IL2, IL4 and IL-17-producing cells was determined by ELISPOT. Results are presented as spot forming units per $10^6$ cells, which were subtracted from the values obtained from non-stimulated cells. The SEM of triplicates is indicated by vertical lines.

FIG. 8: Analysis of the T helper patterns stimulated by Cytometric Bead Array. Culture supernatants from proliferating cells from mice immunized by the (A) i.n. or (B) s.c. routes were collected on days 2 and 4, and stored at −70° C. Determinations of GM-CSF, IFN-gamma, IL-1 alpha, IL-2, IL-4, IL-5, IL-6, IL-10, IL-17 and TNF-alpha were performed by cytometric bead array analysis using the commercial kit from Bender, according to the manufacturer's instructions. A standard curve was generated for each cytokine by using the corresponding recombinant murine cytokines (Bender). Results are expressed as concentration (pg/ml).

FIG. 9: Antigenic epitopes delivered by linking to BPPcysMPEG induce superior CTL response. Mice (n=3) were immunized with BPPcysOva′′′PEG (10 μg/mouse), with OVA (3 mg/mouse)+BPPcysMPEG(3 μg/mouse) or with $OVA_{257-264}$ (10 μg)+$OVA_{323-339}$ (10 μg)+BPPcysMPEG (10 μg/mouse), by giving foot pad injection in two doses at an interval of one week. The CTL response in these mice was compared in an in vivo cytotoxicity assay. The data is represented as mean and SEM of percentage specific lysis of target cells obtained from each group. The result is representative of two independent experiments.

FIG. 10: (A) Overview of novel BPPcysPeptide′′′PEG molecule and the (B) structural formula of the planned BPPcysPeptide′′′PEG compounds in the research area flu. (C) Structural formula of the novel BPPcysPeptide′′′PEG in the research field Dengue fever and (D) Hep B.

The invention claimed is:

1. Lipopeptide-compound or lipoprotein-compound according to formula I, or lipopeptide-conjugate or a lipoprotein-conjugate according to formula I, having an adjuvant moiety, a first antigen moiety, a second antigen moiety and, optionally, a conjugate moiety:

$$R_1-CO-CH_2$$
$$R_2-CO-CH-CH_2-X-CH_2-CH-CO-Y_1-L-Y_2-R_5$$
$$\qquad\qquad\qquad\qquad\qquad\qquad\quad NR_3R_4$$
(I)

wherein $R_1$ and $R_2$ can be identical or different and are selected from $C_{11}$-$C_{17}$ alkyl or $C_{11}$-$C_{17}$ alkenyl groups;

$R_3$ and $R_4$ can be identical or different and are selected from hydrogen or $C_{1-6}$ Alkyl group;

X is S;

$Y_1$ represents a first antigen moiety recognized by a CD4+ T cell and $Y_2$ represents a second antigen moiety recognized by a CD8+ T cell, or vice versa, wherein the size for the CD8+ T cell-recognized antigen moiety is of from 8 to 14 and for the CD4+ T cell-recognized antigen moiety is of from 10 to 20 amino acid residues and wherein $Y_1$ and $Y_2$ represent antigenic epitopes from at least one microorganism causing a parasitic or infectious disease selected from the group consisting of hepatitis B, hepatitis C, acquired immunodeficiency syndrome (AIDS), Dengue fever, influenza, *Helicobacter pylori* infection, herpesvirus infection, tuberculosis, leprosy, listeriosis, malaria, and *Tryopanosoma cruzii* infection, and L is an amino acid sequence of 1 to 3 amino acid residues;

$R_5$ is hydrogen or a covalently linked conjugate moiety comprising polyalkylene glycol units of the formula II $$Z_1-[(CHR_6)_n-O]_x-(CH_2)_2-Z_2 \qquad (II)$$

where $Z_1$ is a hydrocarbon or a $NR_3$ group whereby $R_3$ defined as above, $R_6$ is independently any one of hydrogen, OH, $C_{1-6}$ alkyl group, $OR_7$ or $COR_8$;

$R_7$ is independently any one of hydrogen or $C_{1-6}$ alkyl group;

$R_8$ is independently any one of hydrogen, OH, $OR_7$ or $NR_9R_{10}$;

$R_9$ and $R_{10}$ are independently any one of hydrogen or hydrocarbon which may contain heteroatom (s) and which may form a ring;

x is an integer of 1 to 100;

n is independently an integer of 1 to 10; and $Z_2$ is a hydrogen or a hydrocarbon which may contain heteroatom(s);

wherein Y1-L-Y2 of Formula I, comprising the antigen moieties, has the sequence identity of a sequence selected from the group consisting of SEQ ID NO:1, SEQ ID NO:2, SEQ ID NO:3, SEQ ID NO:4, SEQ ID NO:6, SEQ ID NO:7, or wherein Y1 is an Ig-like domain EIII of a flavivirus envelope glycoprotein E and Y2 is SEQ ID NO:5.

2. The lipopeptide- or lipoprotein-conjugate according to claim 1, wherein n is an integer of 2, 3 or 4, and x is independently therefrom an integer of 15 to 35.

3. The lipopeptide- or lipoprotein-conjugate according to claim 1 wherein $R_5$ represents a monodisperse polyethyleneglycol unit.

4. A pharmaceutical composition comprising a lipopeptide- or a lipoprotein-compound or a lipopeptide- or lipoprotein-conjugate according to claim 1.

5. The pharmaceutical composition according to claim 4 containing at least two different types of said lipopeptide- or lipoprotein-conjugate whereby said at least two different types of said lipopeptide- or lipoprotein-conjugates have the same adjuvant moiety and different antigen moieties.

6. The lipopeptide- or lipoprotein-conjugate of claim 1, wherein L is an amino acid sequence of 2 amino acid residues.

7. The lipopeptide- or lipoprotein-conjugate of claim 1, wherein L is an amino acid sequence of alanines.

8. The lipopeptide- or lipoprotein-conjugate of claim 1, wherein $R_1$ and $R_2$ are identical $C_{15}$ alkyl groups.

9. The lipopeptide- or lipoprotein-conjugate of claim 2, wherein n is 2.

10. The lipopeptide- or lipoprotein-conjugate of claim 2, wherein x is an integer of 20 to 30.

11. The lipopeptide- or lipoprotein-conjugate of claim 2, wherein x is 26.

12. The lipopeptide or lipoprotein conjugate according to claim 1, wherein the antigenic epitopes from at least one microorganism causing an infectious disease are selected from the group consisting of Dengue fever, influenza, hepatitis B, hepatitis C and AIDS.

13. The lipopeptide or lipoprotein conjugate according to claim 1, wherein Y1-L-Y2 of Formula I has the sequence identity of SEQ ID NO:1.

* * * * *